(12) United States Patent
Schuh et al.

(10) Patent No.: US 11,779,421 B2
(45) Date of Patent: Oct. 10, 2023

(54) ARTICULATING MEDICAL INSTRUMENTS

(71) Applicant: Auris Health, Inc., Redwood City, CA (US)

(72) Inventors: Travis Michael Schuh, Los Altos, CA (US); Nicholas J. Eyre, Sunnyvale, CA (US); Alex J. Niswander, Blue Ridge, GA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 17/533,094

(22) Filed: Nov. 22, 2021

(65) Prior Publication Data

US 2022/0087760 A1 Mar. 24, 2022

Related U.S. Application Data

(63) Continuation of application No. 16/580,822, filed on Sep. 24, 2019, now Pat. No. 11,179,212.

(60) Provisional application No. 62/736,643, filed on Sep. 26, 2018.

(51) Int. Cl.
| | | |
|---|---|---|
| *A61B 34/00* | (2016.01) | |
| *A61B 17/00* | (2006.01) | |
| *A61B 34/37* | (2016.01) | |
| *A61B 34/30* | (2016.01) | |

(52) U.S. Cl.
CPC ........ *A61B 34/71* (2016.02); *A61B 17/00234* (2013.01); *A61B 34/37* (2016.02); *A61B 2017/00278* (2013.01); *A61B 2017/00305* (2013.01); *A61B 2017/00809* (2013.01); *A61B 2017/00818* (2013.01); *A61B 2034/301* (2016.02); *A61B 2034/305* (2016.02)

(58) Field of Classification Search
CPC ... A61B 34/71; A61B 17/00234; A61B 34/37; A61B 2017/00305; A61B 2034/301; A61B 2034/305; A61B 2017/00809; A61B 2017/00818; A61B 2017/00314; A61B 2017/00323
USPC .......................................... 600/104, 146, 152
See application file for complete search history.

(56) References Cited

U.S. PATENT DOCUMENTS

| | | | |
|---|---|---|---|
| 3,572,325 A | 3/1971 | Bazell et al. | |
| 3,913,565 A | 10/1975 | Kawahara | |
| 4,294,234 A | 10/1981 | Matsuo | |
| (Continued) | | | |

FOREIGN PATENT DOCUMENTS

| | | |
|---|---|---|
| CN | 1846181 A | 10/2006 |
| CN | 1857877 A | 11/2006 |
| (Continued) | | |

OTHER PUBLICATIONS

International search report and written opinion dated Jan. 17, 2020 for PCT/US2019/052729.

*Primary Examiner* — Wade Miles
*Assistant Examiner* — Bridget E. Rabaglia
(74) *Attorney, Agent, or Firm* — Conley Rose, P.C.

(57) ABSTRACT

Articulating medical instruments and corresponding techniques can be utilized using a robotically enabled medical system. In a surgical method, a clinician can insert a distal end of a medical instrument into a treatment area of a patient. Once inserted, a first bending section of the medical instrument can be articulated by driving one or more motors of an articulation handle that is positioned at a proximal end of the elongated shaft.

19 Claims, 32 Drawing Sheets

(56) References Cited

U.S. PATENT DOCUMENTS

| | | |
|---|---|---|
| 4,392,485 A | 7/1983 | Hiltebrandt |
| 4,607,619 A | 8/1986 | Seike et al. |
| 4,690,175 A | 9/1987 | Ouchi et al. |
| 4,706,656 A | 11/1987 | Kubota |
| 4,741,326 A | 5/1988 | Sidall |
| 4,745,908 A | 5/1988 | Wardle |
| 4,748,969 A | 6/1988 | Wardle |
| 4,750,475 A | 6/1988 | Yoshihashi |
| 4,771,766 A | 9/1988 | Aoshiro |
| 4,846,791 A | 7/1989 | Hattier et al. |
| 4,869,238 A | 9/1989 | Opie et al. |
| 4,906,496 A | 3/1990 | Hosono et al. |
| 4,907,168 A | 3/1990 | Boggs |
| 4,941,455 A * | 7/1990 | Watanabe ............ A61B 1/0052 600/146 |
| 4,967,732 A | 11/1990 | Inoue |
| 5,050,585 A | 9/1991 | Takahashi |
| 5,083,549 A | 1/1992 | Cho et al. |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,217,002 A | 6/1993 | Katsurada |
| 5,251,611 A | 10/1993 | Zehel |
| 5,257,617 A | 11/1993 | Takahashi |
| 5,261,391 A | 11/1993 | Inoue |
| 5,287,861 A | 2/1994 | Wilk |
| 5,313,934 A | 5/1994 | Wiita et al. |
| 5,386,818 A | 2/1995 | Schneebaum |
| 5,448,988 A | 9/1995 | Watanabe |
| 5,478,330 A | 12/1995 | Imran et al. |
| 5,482,029 A | 1/1996 | Sekiguchi |
| 5,489,270 A | 2/1996 | van Erp |
| 5,507,725 A | 4/1996 | Savage et al. |
| 5,533,985 A | 7/1996 | Wang |
| 5,580,200 A | 12/1996 | Fullerton |
| 5,681,296 A | 10/1997 | Ishida |
| 5,704,534 A | 1/1998 | Huitema et al. |
| 5,720,775 A | 2/1998 | Lmard |
| 5,741,429 A | 4/1998 | Donadio, III |
| 5,749,889 A | 5/1998 | Bacich et al. |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan |
| 5,888,191 A | 3/1999 | Akiba |
| 5,910,129 A | 6/1999 | Koblish |
| 5,938,586 A | 8/1999 | Wilk et al. |
| 5,938,587 A | 8/1999 | Taylor et al. |
| 6,012,494 A | 1/2000 | Balazs |
| 6,143,013 A | 11/2000 | Samson |
| 6,157,853 A | 12/2000 | Blume et al. |
| 6,174,280 B1 | 1/2001 | Oneda |
| 6,197,015 B1 | 3/2001 | Wilson |
| 6,198,974 B1 | 3/2001 | Webster, Jr. |
| 6,234,958 B1 | 5/2001 | Snoke et al. |
| 6,315,715 B1 | 11/2001 | Taylor et al. |
| 6,404,497 B1 | 6/2002 | Backman |
| 6,436,107 B1 | 8/2002 | Wang et al. |
| 6,464,632 B1 | 10/2002 | Taylor |
| 6,485,411 B1 | 11/2002 | Konstorum |
| 6,491,626 B1 | 12/2002 | Stone et al. |
| 6,537,205 B1 | 3/2003 | Smith |
| 6,554,793 B1 | 4/2003 | Pauker et al. |
| 6,716,178 B1 | 4/2004 | Kilpatrick et al. |
| 6,746,422 B1 | 6/2004 | Noriega |
| 6,749,560 B1 | 6/2004 | Konstorum |
| 6,790,173 B2 | 9/2004 | Saadat |
| 6,827,710 B1 | 12/2004 | Mooney et al. |
| 6,827,712 B2 | 12/2004 | Tovey et al. |
| 6,837,846 B2 | 1/2005 | Jaffe |
| 6,908,428 B2 | 6/2005 | Aizenfeld |
| 6,921,362 B2 | 7/2005 | Ouchi |
| 6,958,035 B2 | 10/2005 | Friedman et al. |
| 7,008,401 B2 | 3/2006 | Thompson et al. |
| 7,130,700 B2 | 10/2006 | Gardeski et al. |
| 7,594,903 B2 | 9/2009 | Webler et al. |
| 7,645,230 B2 | 1/2010 | Mikkaichi |
| 7,645,231 B2 | 1/2010 | Akiba |
| 7,789,827 B2 | 9/2010 | Landry |
| 7,930,065 B2 | 4/2011 | Larkin et al. |
| 8,046,049 B2 | 10/2011 | Govari et al. |
| 8,052,636 B2 | 11/2011 | Moll et al. |
| 8,246,536 B2 | 8/2012 | Ochi |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura |
| 8,686,747 B2 | 4/2014 | Berner |
| 8,740,885 B2 * | 6/2014 | Larkin ................ A61B 1/04 606/1 |
| 8,758,231 B2 | 6/2014 | Bunch et al. |
| 8,827,947 B2 | 9/2014 | Bosman et al. |
| 9,186,046 B2 | 11/2015 | Ramamurthy et al. |
| 9,314,953 B2 | 4/2016 | Lauer |
| 9,427,551 B2 | 8/2016 | Leeflang et al. |
| 9,504,604 B2 | 11/2016 | Alvarez |
| 9,561,083 B2 | 2/2017 | Yu et al. |
| 9,591,990 B2 | 3/2017 | Chen et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,463,439 B2 | 11/2019 | Joseph et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |

(56) References Cited

U.S. PATENT DOCUMENTS

| | | |
|---|---|---|
| 10,539,478 B2 | 1/2020 | Lin |
| 10,543,048 B2 | 1/2020 | Noonan et al. |
| 10,639,114 B2 | 5/2020 | Schuh |
| 10,765,487 B2 | 9/2020 | Ho |
| 2001/0004676 A1 | 6/2001 | Ouchi |
| 2003/0036748 A1 | 2/2003 | Cooper |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0193013 A1 | 9/2004 | Isakawa et al. |
| 2004/0249246 A1 | 12/2004 | Campos |
| 2005/0004515 A1 | 1/2005 | Hart et al. |
| 2005/0107667 A1 | 5/2005 | Danitz |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0165366 A1 | 7/2005 | Brustad |
| 2005/0222581 A1 | 10/2005 | Fischer et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2007/0055219 A1 | 3/2007 | Whitman |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0147089 A1 | 6/2008 | Loh |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2009/0099420 A1 | 4/2009 | Woodley et al. |
| 2009/0163851 A1 | 6/2009 | Holloway |
| 2009/0240110 A1 | 9/2009 | Miyawaki |
| 2009/0247880 A1 | 10/2009 | Naruse et al. |
| 2009/0254083 A1 | 10/2009 | Wallace et al. |
| 2009/0299344 A1 | 12/2009 | Lee et al. |
| 2009/0306587 A1 | 12/2009 | Milijasevic et al. |
| 2009/0326325 A1 | 12/2009 | Naito |
| 2010/0030023 A1 | 2/2010 | Yoshie |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0168918 A1 | 7/2010 | Zhao |
| 2010/0217184 A1 | 8/2010 | Koblish et al. |
| 2010/0249497 A1 | 9/2010 | Peine |
| 2010/0249506 A1 | 9/2010 | Prisco et al. |
| 2011/0009863 A1 | 1/2011 | Stanislaw |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0245844 A1 | 10/2011 | Jinno et al. |
| 2011/0261183 A1 | 10/2011 | Ma et al. |
| 2011/0306836 A1 | 12/2011 | Ohline et al. |
| 2012/0071894 A1 | 3/2012 | Tanner et al. |
| 2012/0071895 A1 | 3/2012 | Stabler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0204124 A1 | 8/2013 | Duindam |
| 2013/0226151 A1 | 8/2013 | Suehara |
| 2013/0303892 A1 | 11/2013 | Zhao |
| 2013/0304091 A1 | 11/2013 | Straehnz et al. |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012288 A1 | 1/2014 | Darisse |
| 2014/0046313 A1 | 2/2014 | Pederson et al. |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0276594 A1 | 9/2014 | Tanner et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2015/0031950 A1 | 1/2015 | Drontle et al. |
| 2015/0255782 A1 | 9/2015 | Kim et al. |
| 2016/0000414 A1 | 1/2016 | Brown |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0183841 A1 | 6/2016 | Duindam et al. |
| 2016/0227982 A1 | 8/2016 | Takahashi |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0056118 A1* | 3/2017 | Cooper ............... B25J 15/0475 |
| 2017/0119481 A1 | 5/2017 | Romo et al. |
| 2017/0281218 A1 | 5/2017 | Timm |
| 2017/0165011 A1 | 6/2017 | Bovay et al. |
| 2017/0189128 A1* | 7/2017 | Auld ..................... A61B 34/30 |
| 2017/0202627 A1 | 7/2017 | Sramek et al. |
| 2017/0209073 A1 | 7/2017 | Sramek et al. |
| 2017/0239005 A1* | 8/2017 | Cohen ................... A61B 17/29 |
| 2017/0290631 A1 | 10/2017 | Lee et al. |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0214011 A1 | 8/2018 | Graetzel et al. |
| 2018/0214220 A1 | 8/2018 | Kan |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |

(56) References Cited

U.S. PATENT DOCUMENTS

| | | |
|---|---|---|
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0110839 A1 | 4/2019 | Rafii-Tari et al. |
| 2019/0110843 A1 | 4/2019 | Ummalaneni et al. |
| 2019/0151148 A1 | 5/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0307987 A1 | 10/2019 | Yu |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054408 A1 | 2/2020 | Schuh et al. |
| 2020/0060516 A1 | 2/2020 | Baez |
| 2020/0093549 A1 | 3/2020 | Chin |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 102316817 A | 1/2012 |
| CN | 102458295 A | 5/2012 |
| CN | 102665590 A | 9/2012 |
| CN | 102711586 A | 10/2012 |
| CN | 102973317 A | 3/2013 |
| CN | 103767659 A | 5/2014 |
| CN | 103930063 A | 7/2014 |
| EP | 0543539 | 5/1993 |
| EP | 0776739 | 6/1997 |
| EP | 0904796 | 3/1999 |
| EP | 1442720 | 8/2004 |
| EP | 2130478 B1 | 7/2013 |
| JP | 2006525087 A | 11/2006 |
| JP | 2007511247 A | 5/2007 |
| JP | 2010046384 A | 3/2010 |
| JP | 2011015992 A | 1/2011 |
| JP | 2012105793 A | 6/2012 |
| WO | WO-1994014494 A2 | 7/1994 |
| WO | WO-2000067640 A2 | 11/2000 |
| WO | WO-2002074178 A2 | 9/2002 |
| WO | WO-2004039273 A2 | 5/2004 |
| WO | WO-2004105849 A1 | 12/2004 |
| WO | WO-2005032637 A2 | 4/2005 |
| WO | WO-2005081202 A1 | 9/2005 |
| WO | WO-2007146987 A2 | 12/2007 |
| WO | WO-2008097540 A2 | 8/2008 |
| WO | WO-2009092059 A2 | 7/2009 |
| WO | WO-2009097461 A1 | 8/2009 |
| WO | WO-2010081187 A1 | 7/2010 |
| WO | WO-2011005335 A1 | 1/2011 |
| WO | WO-2013107468 A1 | 7/2013 |
| WO | WO-2015093602 A1 | 6/2015 |
| WO | WO-2016003052 A1 | 1/2016 |

\* cited by examiner

ARTICULATING MEDICAL INSTRUMENTS

CROSS-REFERENCE TO RELATED APPLICATIONS

This application is a continuation of U.S. patent application Ser. No. 16/580,822, filed on Sep. 24, 2019, which claims priority to U.S. Provisional Patent Application No. 62/736,643, filed Sep. 26, 2018, which is incorporated herein by reference. Any and all application(s) for which a foreign or domestic priority claim is identified in the Application Data Sheet as filed with the present application are hereby incorporated by reference under 37 CFR 1.57.

TECHNICAL FIELD

The systems and methods disclosed herein are directed to medical instruments, and more particularly, to articulating medical instruments that can be configured for use during robotic medical procedures.

BACKGROUND

Medical procedures, such as laparoscopy, may involve accessing and visualizing an internal region of a patient. In a laparoscopic procedure, a medical instrument can be inserted into the internal region through a laparoscopic access port.

In certain procedures, a robotically enabled medical system may be used to control the insertion and/or manipulation of the instrument and end effector thereof. The robotically enabled medical system may include a robotic arm, or other instrument positioning device. The robotically enabled medical system may also include a controller used to control the positioning of the instrument during the procedure.

SUMMARY

The systems, methods and devices of this disclosure each have several innovative aspects, no single one of which is solely responsible for the desirable attributes disclosed herein.

In a first aspect, a medical instrument includes an elongate shaft extending between a proximal end and a distal end; a first bending section positioned between the proximal end and the distal end of the elongate shaft; an articulation handle positioned at the proximal end of the shaft; and one or motors positioned within the articulation handle and configured to articulate the first bending section.

In some embodiments, the medical instrument may also include one or more of the following features in any combination: (a) an insertion handle coupled to the shaft, wherein the insertion handle is configured to cause translation of the shaft relative to the insertion handle; (b) wherein the first bending section comprises a multi-link wrist, the multi-link wrist comprising two or more links, each pair of consecutive links including one or more joints therebetween; (c) wherein each of the one or more joints comprise a rolling joint; (d) the first bending section comprises a proximal pitch joint and a distal pitch joint configured to allow articulation of the first bending section in a pitch direction, and the articulation handle comprises a proximal pitch pulley connected to the proximal pitch joint by a first pull wire, and a distal pitch pulley connected to the distal pitch joint by a second pull wire, wherein a distal pitch pulley radius of the distal pitch pulley is greater than a proximal pitch pulley radius of the proximal pitch pulley; (e) the first bending section comprises a proximal pitch joint and a distal pitch joint configured to allow articulation of the first bending section in a pitch direction, and the articulation handle comprises a proximal pitch pulley connected to the proximal pitch joint by a first pull wire, and a distal pitch pulley connected to the distal pitch joint by a second pull wire, wherein a distal pitch pulley radius is different than a proximal pitch pulley radius such that the proximal pitch joint and the distal pitch joint change at substantially the same rate under actuation of the proximal pitch pulley and the distal pitch pulley; (f) wherein the one or more motors positioned within the articulation handle comprise at least one pitch motor configured to drive the proximal pitch pulley and the distal pitch pulley such that rotation of the proximal pitch pulley is of substantially equal rotation to the distal pitch pulley; (g) wherein a ratio between the distal pitch pulley radius and the proximal pitch pulley radius is such that an articulation of the proximal pitch joint is substantially equal to an articulation of the distal pitch joint; (h) wherein the first bending section comprises a proximal yaw joint and a distal yaw joint configured to allow articulation of the first bending section in a yaw direction, and the articulation handle comprises a proximal yaw pulley connected to the proximal yaw joint by a third pull wire, and a distal yaw pulley connected to the distal yaw joint by a fourth pull wire, and wherein a distal yaw pulley radius of the distal yaw pulley is greater than a proximal yaw pulley radius of the proximal yaw pulley; (i) wherein the one or more motors positioned within the articulation handle comprise a yaw motor configured to drive the proximal yaw pulley and the distal yaw pulley such that rotation of the proximal yaw pulley is of substantially equal rotation to the yaw pitch pulley; (j) wherein a ratio between the distal yaw pulley radius and the proximal yaw pulley is such that an articulation of the proximal yaw joint is substantially equal to an articulation of the distal yaw joint; (k) wherein the first bending section comprises one or more links comprising articulation holes configured to receive pull wires extending therethrough; (l) wherein at least one of the links includes a first articulation hole for receiving a first pull wire therethrough and a second articulation hole for receiving a second pull wire therethrough, and the first articulation hole and the second articulation hole are formed at a same angle relative to a central axis through the link and comprise different radii measured from the central axis; (m) wherein at least one of the links includes a first articulation hole for receiving a first pull wire therethrough and a second articulation hole for receiving a second pull wire therethrough, and the first articulation hole and the second articulation hole each have a distance from a pitch articulation axis and a yaw articulation axis that is substantially the same; (n) wherein the first bending section comprises at least four degrees of freedom; (o) wherein the four degrees of freedom comprise a proximal pitch, a distal pitch, a proximal yaw, and a distal yaw; (p) wherein the shaft comprises at least three shaft sections, and the medical instrument further comprises a second bending section between at least two of the shaft sections; (q) wherein a pair of pull wires extends from the articulation section, through the second bending section, and to the first bending section; (r) wherein the pair of pull wires cross each other between the second bending section and the first bending section; (s) wherein the medical instrument comprises a sealed architecture; (t) wherein the medical instrument comprises an endoscope; and/or (u) an optical system for providing an image captured at the distal end of the shaft.

In another aspect, a method includes inserting a distal end of a medical instrument comprising an elongate shaft into a treatment area of a patient; and articulating a first bending section of the medical instrument by driving one or more motors positioned within an articulation handle positioned at a proximal end of the elongated shaft.

The method may include one or more of the following features in any combination: (a) wherein the articulation handle comprises a pitch motor, and the method further comprises driving the one or more motors positioned within the articulation handles comprises using the pitch motor to drive (i) a proximal pitch pulley connected to a proximal pitch joint of the first bending section by a first pull wire, and (ii) a distal pitch pulley connected to a distal pitch joint of the first bending section by a second pull wire, and wherein a distal pitch pulley radius of the distal pitch pulley is different than a proximal pitch pulley radius of the proximal pitch pulley; (b) wherein the pitch motor is configured to drive the proximal pitch pulley and the distal pitch pulley such that rotation of the proximal pitch pulley is of substantially equal rotation to the distal pitch pulley; (c) wherein a ratio between the distal pitch pulley radius and the proximal pitch pulley radius is such that an articulation of the proximal pitch joint is substantially equal to an articulation of the distal pitch joint; (d) wherein driving the one or more motors positioned within the articulation handles further comprises driving, with a yaw motor, a proximal yaw pulley operably connected to a proximal yaw joint of the first bending section by a third pull wire, and a distal yaw pulley operably connected to a distal yaw joint of the first bending section by a fourth pull wire, wherein a distal yaw pulley radius of the distal yaw pulley is different than a proximal yaw pulley radius of the proximal yaw pulley; (e) wherein the yaw motor is configured to drive the proximal yaw pulley and the distal yaw pulley such that rotation of the proximal yaw pulley is of substantially equal rotation to the yaw pitch pulley; (f) wherein a ratio between the distal yaw pulley radius and the proximal yaw pulley radius is such that an articulation of the proximal yaw joint is equal to an articulation of the distal yaw joint; (g) wherein articulating the first bending section comprises pulling a first pull wire that passes through a first articulation hole in a link of the first bending section, and pulling a second pull wire that passes through a second articulation hole in the link of the first bending section, wherein the first articulation hole and the second articulation hole are formed at a same angle relative to a central axis through the link and comprise different radii measured from the central axis; (h) wherein pulling the first pull wire comprises rotating a proximal pulley on which the first pull wire is wound, and pulling the second pull wire comprises rotating a distal pulley on which the second pull wire is wound, wherein a distal pulley radius of the distal pulley is greater than a proximal pulley radius of the proximal pulley; (i) wherein the proximal pulley and the distal pulley are driven by the same motor such that rotation of the proximal pulley is equal to rotation of the distal pulley; and/or (j) articulating a second bending section on the shaft of the medical instrument by driving one or more motors positioned within the articulation handle, wherein the second bending section is positioned between the first bending section and the proximal end.

In another aspect, a medical instrument includes an elongate shaft extending between a proximal end and a distal end; a first bending section positioned between the proximal end and distal end of the elongated shaft; a first handle positioned at the proximal end of the shaft and configured to control articulation of the first bending section; and a second handle coupled to the shaft and configured to facilitate translation of the shaft relative to the second handle.

The medical instrument may also include one or more of the following features in any combination: (a) wherein the first handle comprises one or more motors configured for articulation of the first bending section; (b) wherein the elongate shaft comprises at least three shaft sections, and the medical instrument further comprises a second bending section positioned between at two shaft sections of the shaft; (c) wherein the first handle comprises one or more motors in the first handle that can articulate the first bending section and/or the second bending section; (d) wherein the second handle is configured to couple to an instrument drive mechanism; (e) wherein the second handle comprises at least one drive input configured to engage at least one drive output on the instrument drive mechanism; (f) wherein the medical instrument comprises a sealed architecture; (g) wherein the medical instrument comprises an endoscope; and/or (h) an optical system for providing an image captured at the distal end of the shaft.

In another aspect, a medical instrument includes an elongate shaft extending between a proximal end and a distal end, the shaft comprising at least two shaft sections; a first bending section positioned between that at least two shaft sections of the shaft, the first bending section comprising a proximal pitch joint and a distal pitch joint configured to allow articulation of the first bending section in a pitch direction; an articulation handle positioned at the proximal end of the shaft; a proximal pitch pulley connected to the proximal pitch joint by a first pull wire; and a distal pitch pulley connected to the distal pitch joint by a second pull wire; wherein a distal pitch pulley radius of the distal pitch pulley is different than a proximal pitch pulley radius of the proximal pitch pulley.

The medical instrument may also include one or more of the following features in any combination: (a) a pitch motor positioned within the articulation handle; (b) wherein a ratio between the distal pitch pulley radius and the proximal pitch pulley radius is such that an articulation of the proximal pitch joint is equal to an articulation of the distal pitch joint; (c) wherein the pitch motor is configured to drive the proximal pitch pulley and the distal pitch pulley such that rotation of the proximal pitch pulley is of substantially equal rotation to the distal pitch pulley; (d) wherein the first bending section further comprises a proximal yaw joint and a distal yaw joint configured to allow articulation of the first bending section in a yaw, and the medical instrument further comprises a proximal yaw pulley connected to the proximal yaw joint by a third pull wire, a distal yaw pulley connected to the distal yaw joint by a fourth pull wire, and wherein a distal yaw pulley radius of the distal yaw pulley is greater than a proximal yaw pulley radius of the proximal yaw pulley; (e) a yaw motor positioned within the articulation handle; (f) wherein a ratio between the distal yaw pulley radius and the proximal yaw pulley radius is such that an articulation of the proximal yaw joint is substantially equal to an articulation of the distal yaw joint; (g) wherein the yaw motor is configured to drive the proximal yaw pulley and the distal yaw pulley such that rotation of the proximal yaw pulley is equal rotation of the distal yaw pulley; (h) a second bending section operatively coupled to the first bending section; (i) wherein the first pull wire and the second pull wire extend through the second bending section to the first bending section; (j) wherein, in the second bending section, the first pull wire has a distance from a midline of the shaft that is larger than a distance of the second pull wire from the midline of the shaft, and wherein in the first bending section, the first pull wire has a distance from the midline of the shaft that is smaller than a distance of the second pull wire from the midline of the shaft; and/or (k) an insertion handle coupled to the shaft, wherein the insertion handle is configured to cause translation of the shaft relative to the insertion handle.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 26A illustrates an embodiment that includes articulation holes formed at a constant radius but different angles. FIGS. 26B-26D illustrate an embodiment that includes articulation holes formed at a constant angle but different radii.

DETAILED DESCRIPTION

1. Overview

Aspects of the present disclosure may be integrated into a robotically enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
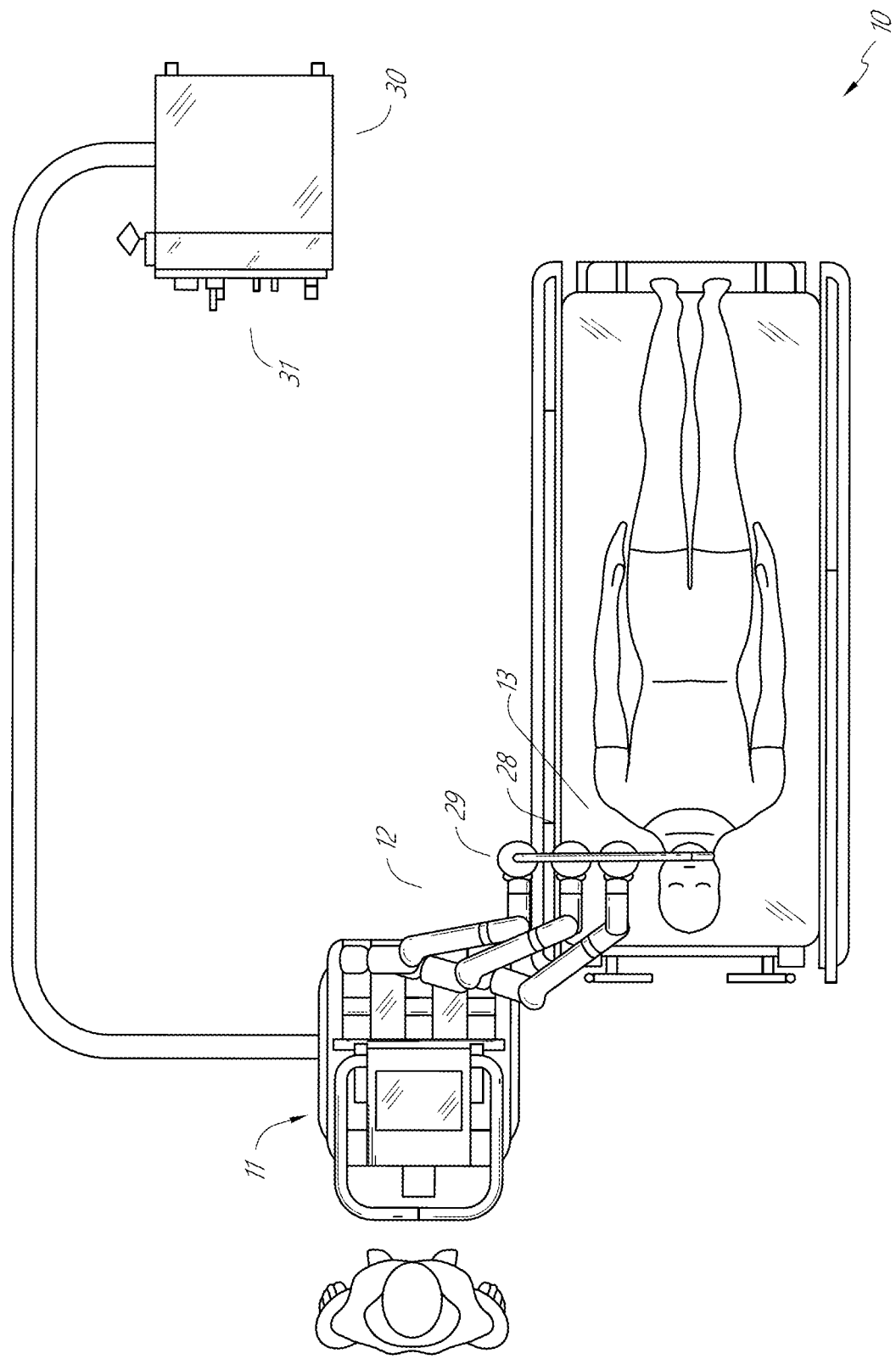
FIG. 1 illustrates an embodiment of a cart-based robotic system arranged for diagnostic and/or therapeutic bronchoscopy.
Figure 2:
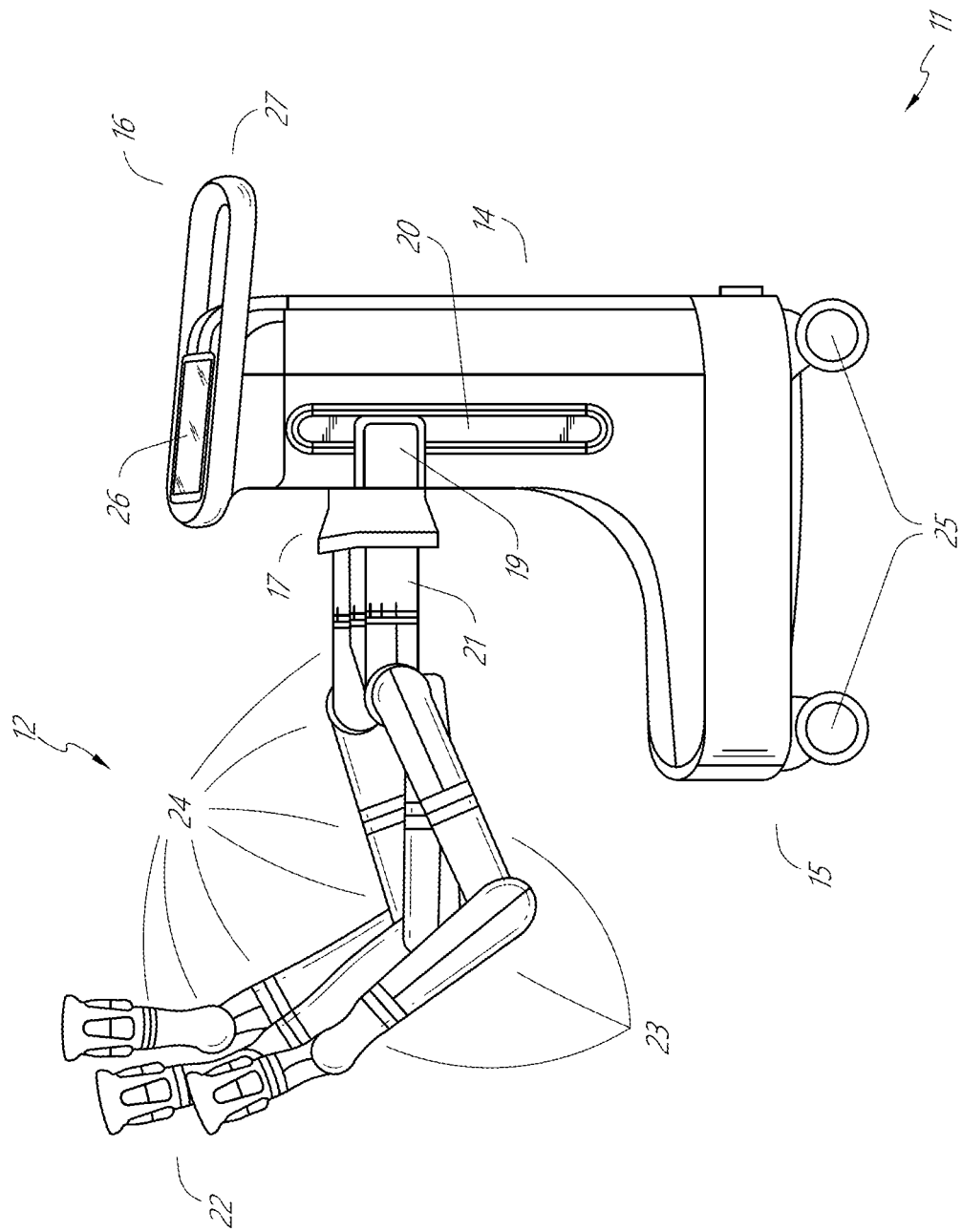
FIG. 2 depicts further aspects of the robotic system of FIG. 1.

The robotically enabled medical system may be configured in a variety of ways depending on the particular procedure. FIG. 1 illustrates an embodiment of a cart-based robotically enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
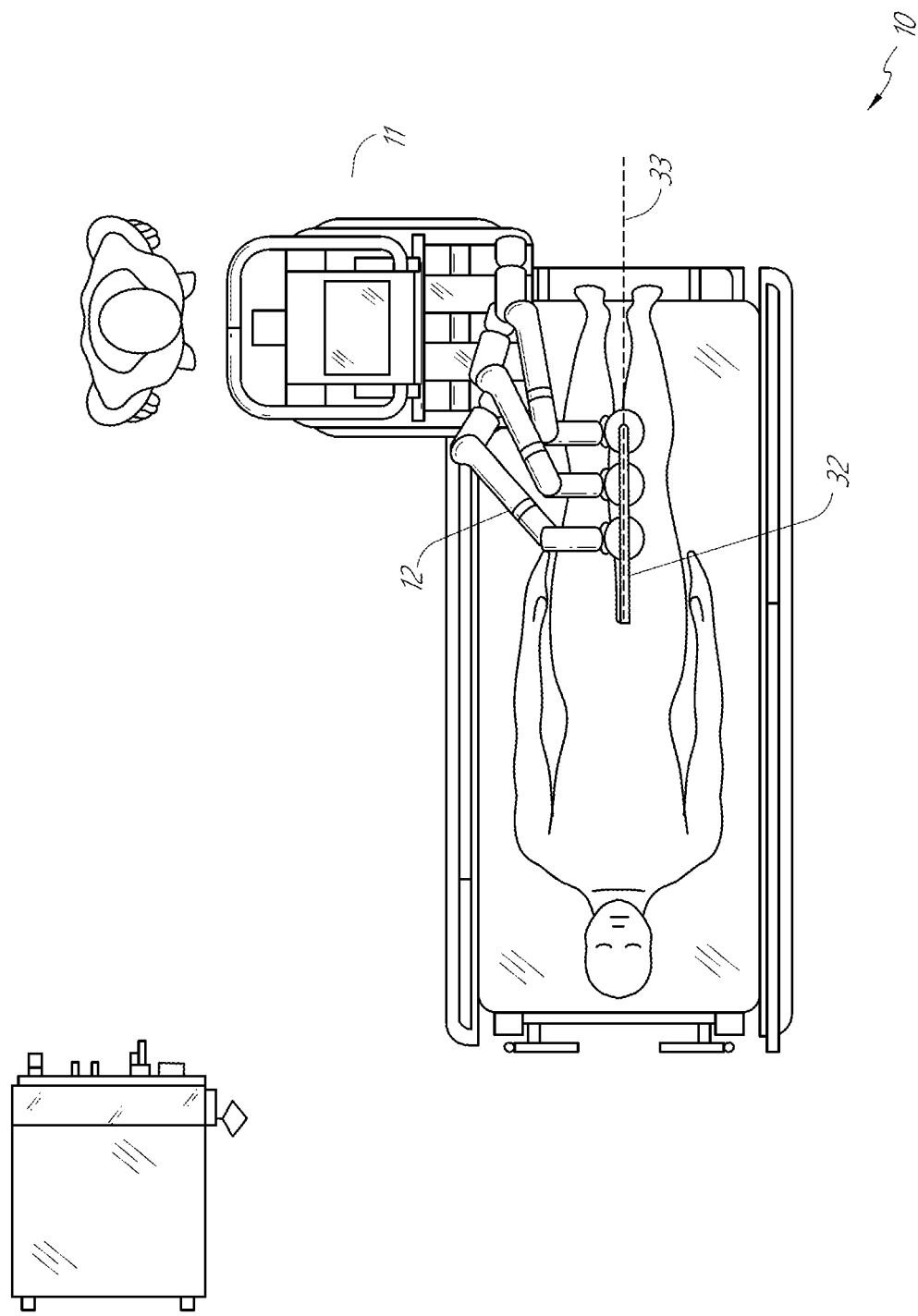
FIG. 3 illustrates an embodiment of the robotic system of FIG. 1 arranged for ureteroscopy.

FIG. 3 illustrates an embodiment of a robotically enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
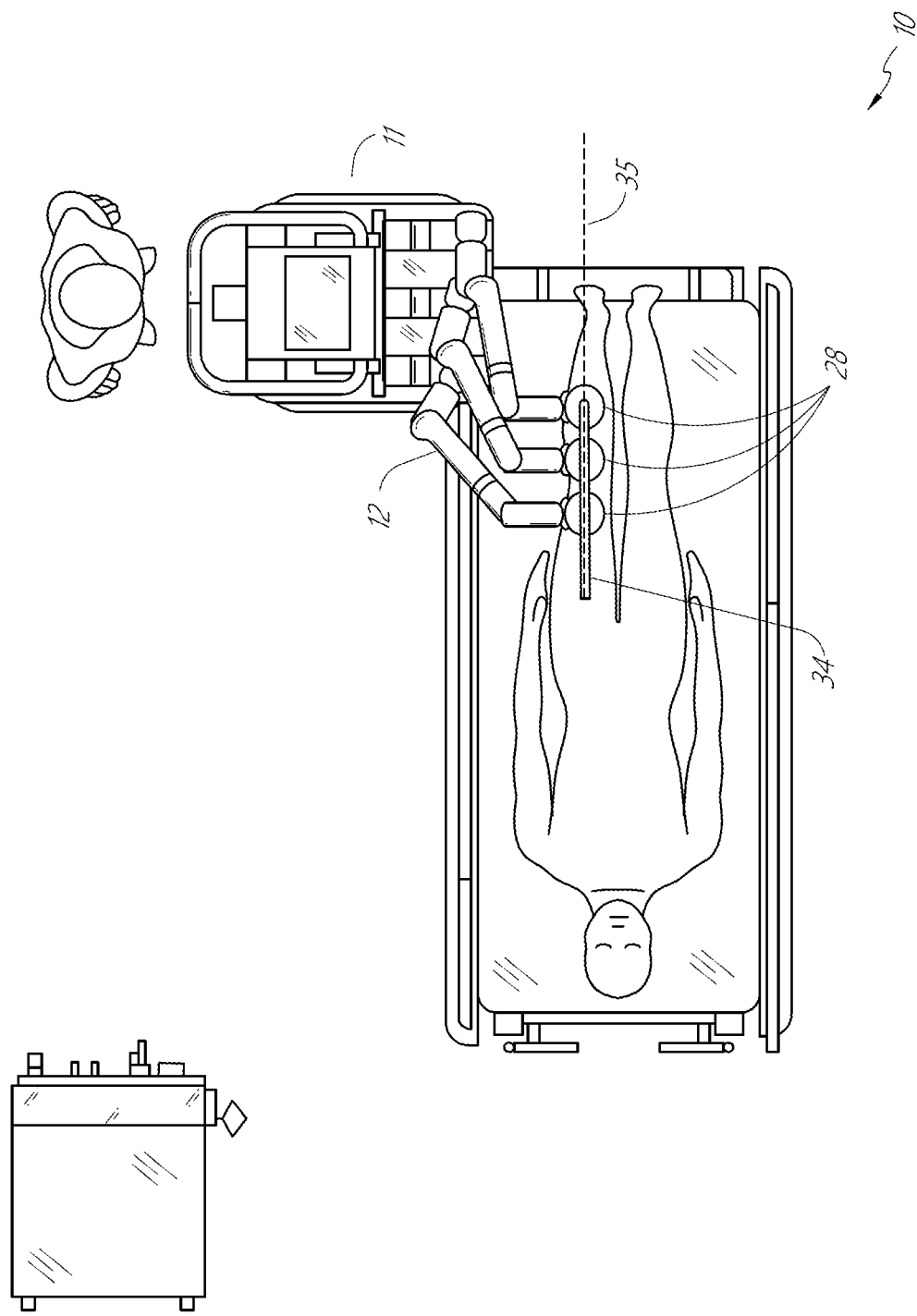
FIG. 4 illustrates an embodiment of the robotic system of FIG. 1 arranged for a vascular procedure.

FIG. 4 illustrates an embodiment of a robotically enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
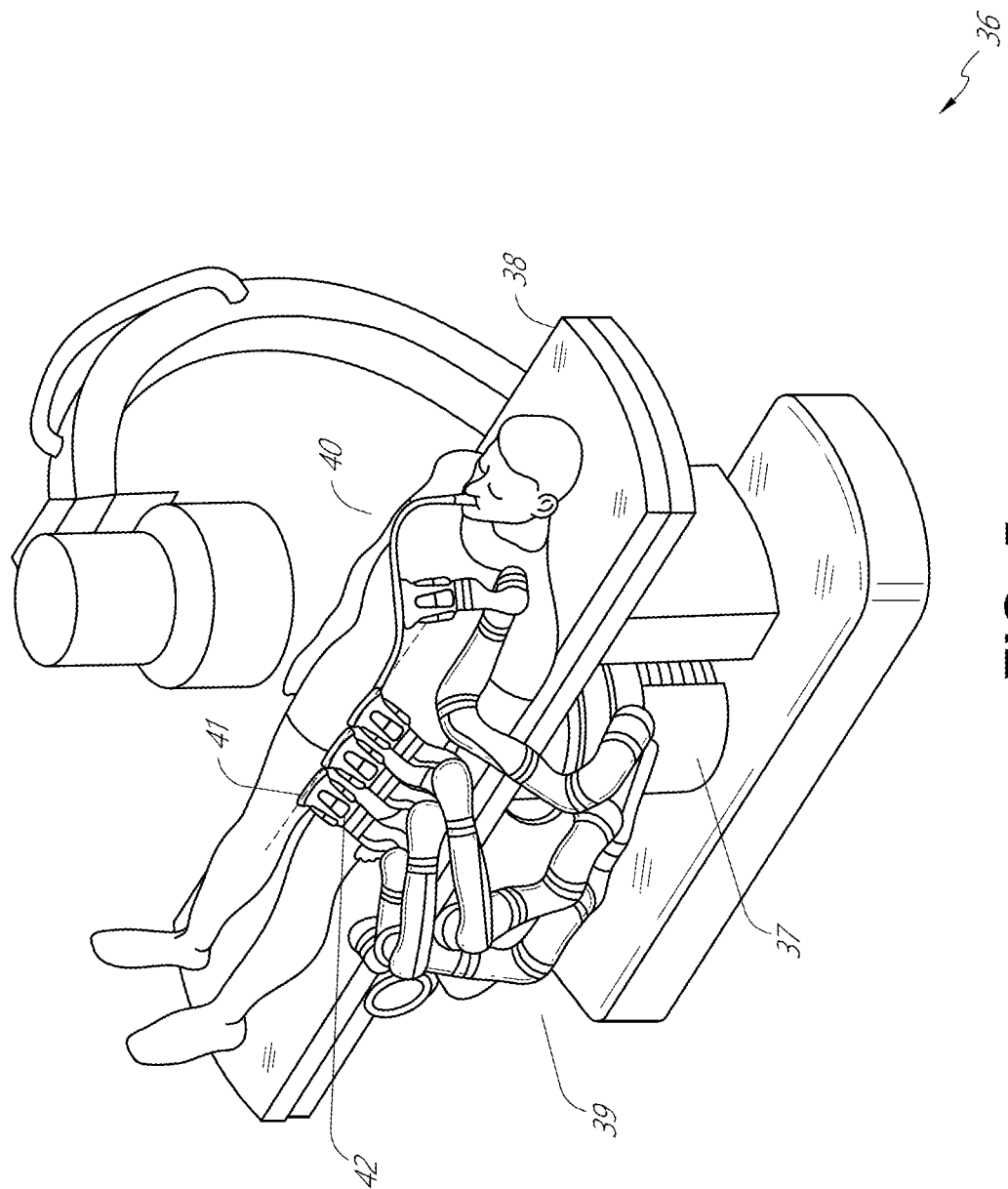
FIG. 5 illustrates an embodiment of a table-based robotic system arranged for a bronchoscopic procedure.

Embodiments of the robotically enabled medical system may also incorporate the patient's table. Incorporation of the table reduces the amount of capital equipment within the operating room by removing the cart, which allows greater access to the patient. FIG. 5 illustrates an embodiment of such a robotically enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
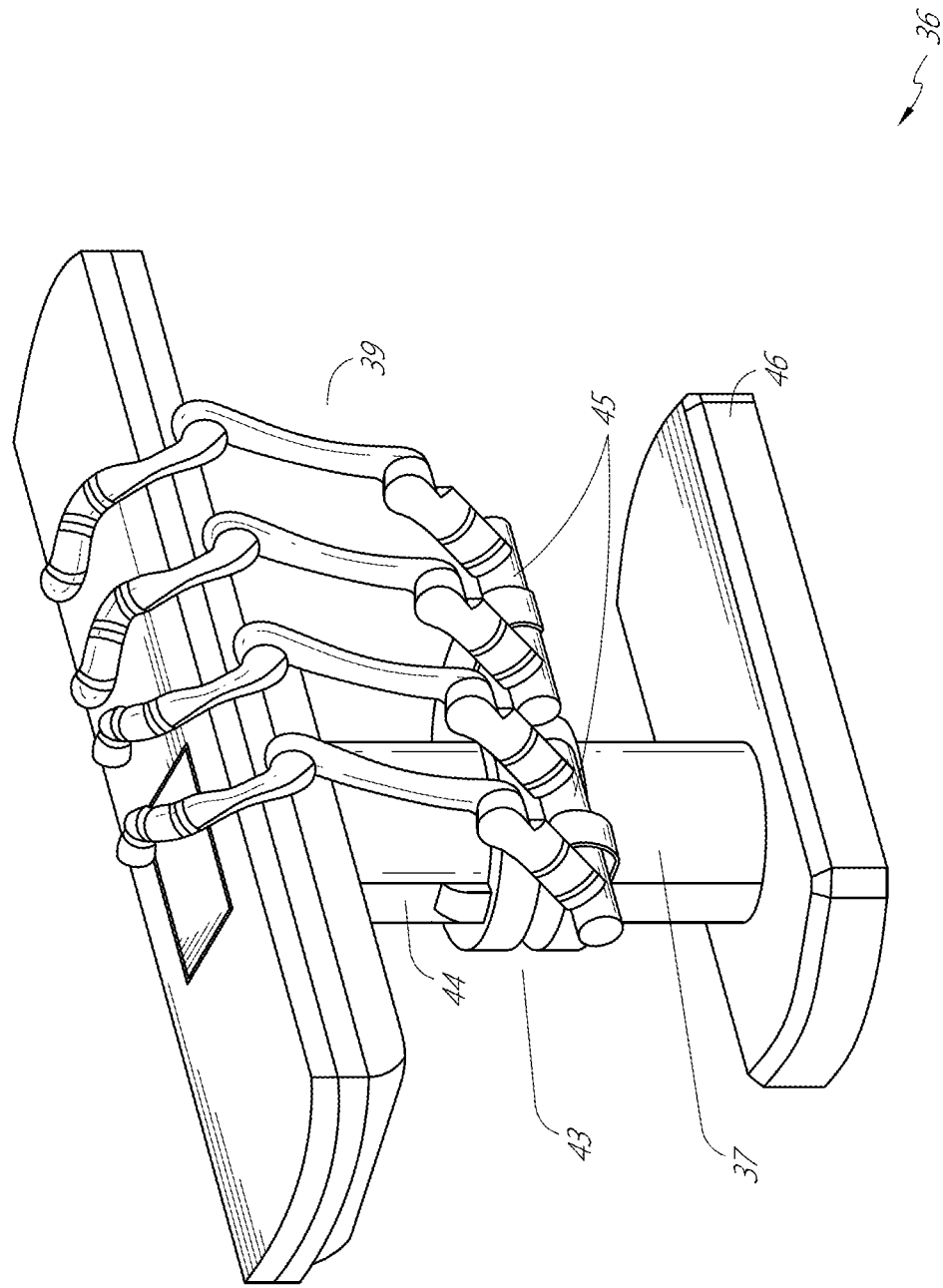
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
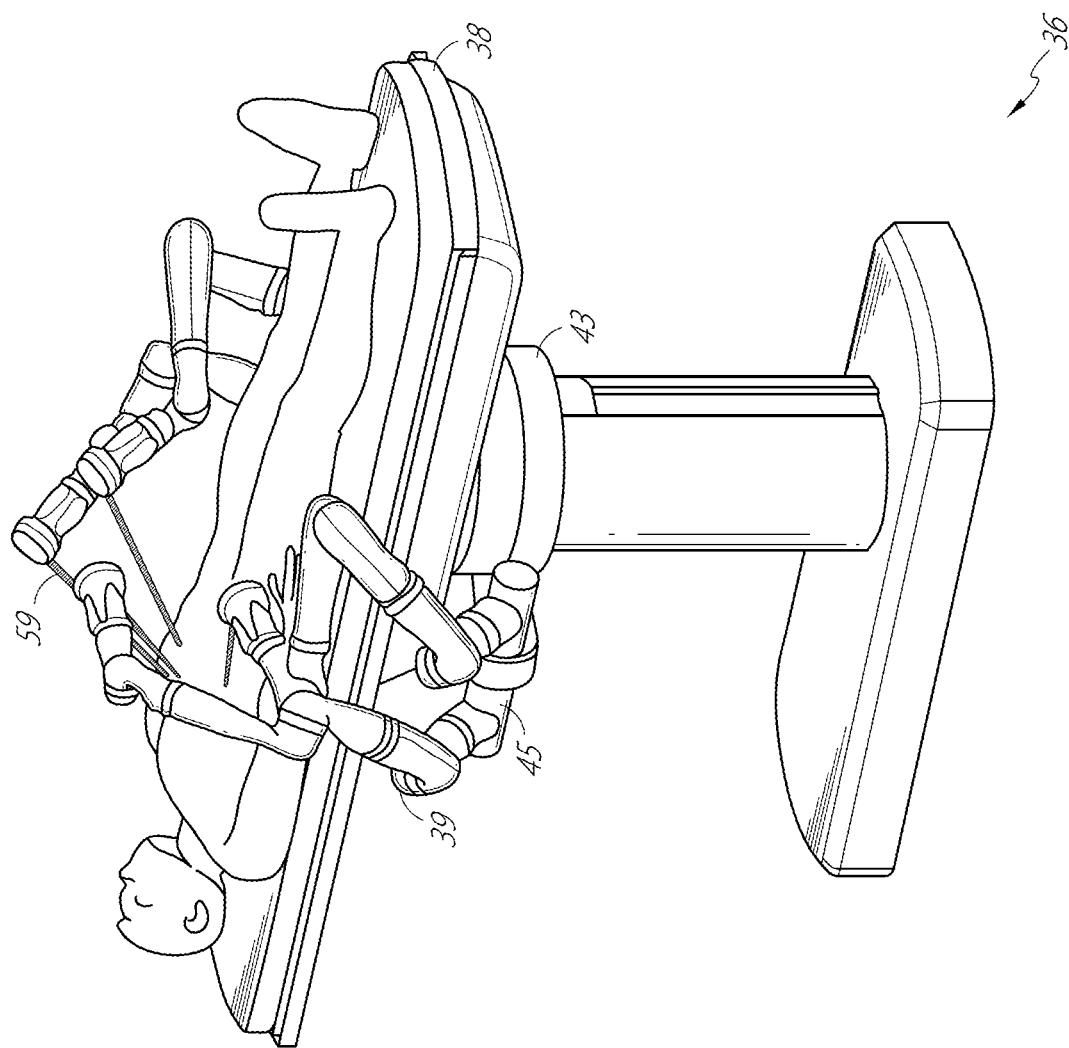
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
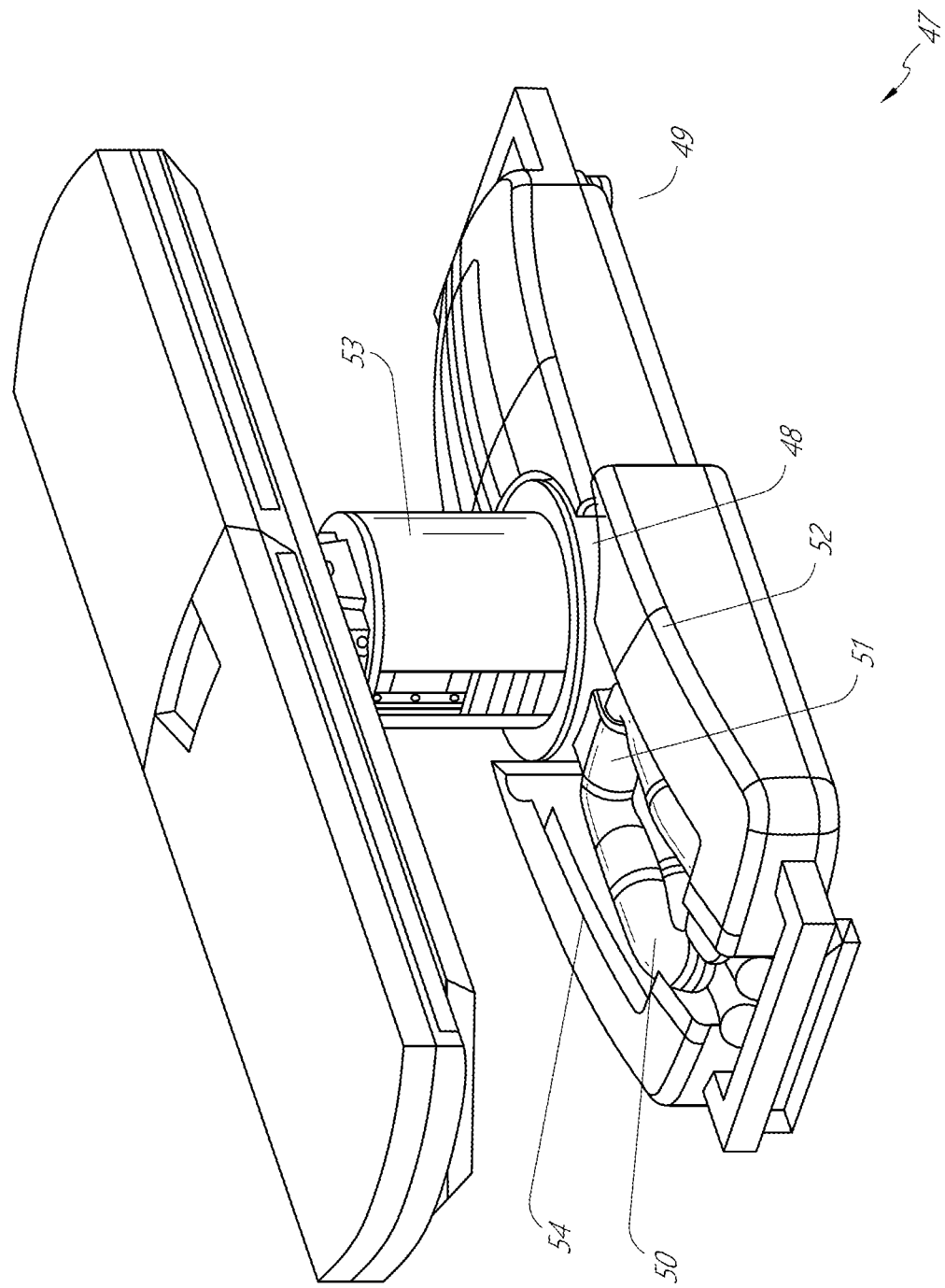
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
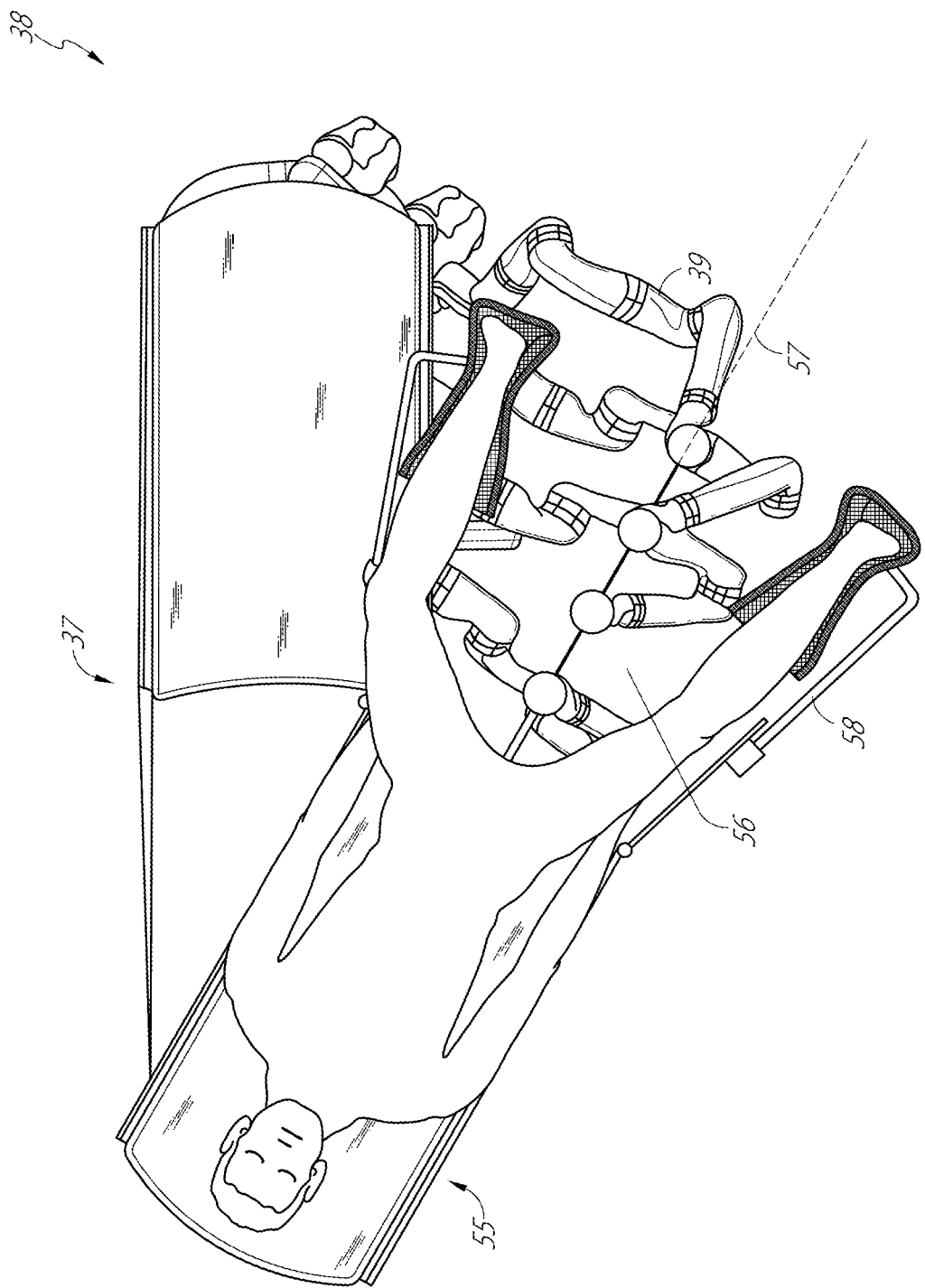
FIG. 8 illustrates an embodiment of a table-based robotic system configured for a ureteroscopic procedure.

FIG. 8 illustrates an embodiment of a robotically enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
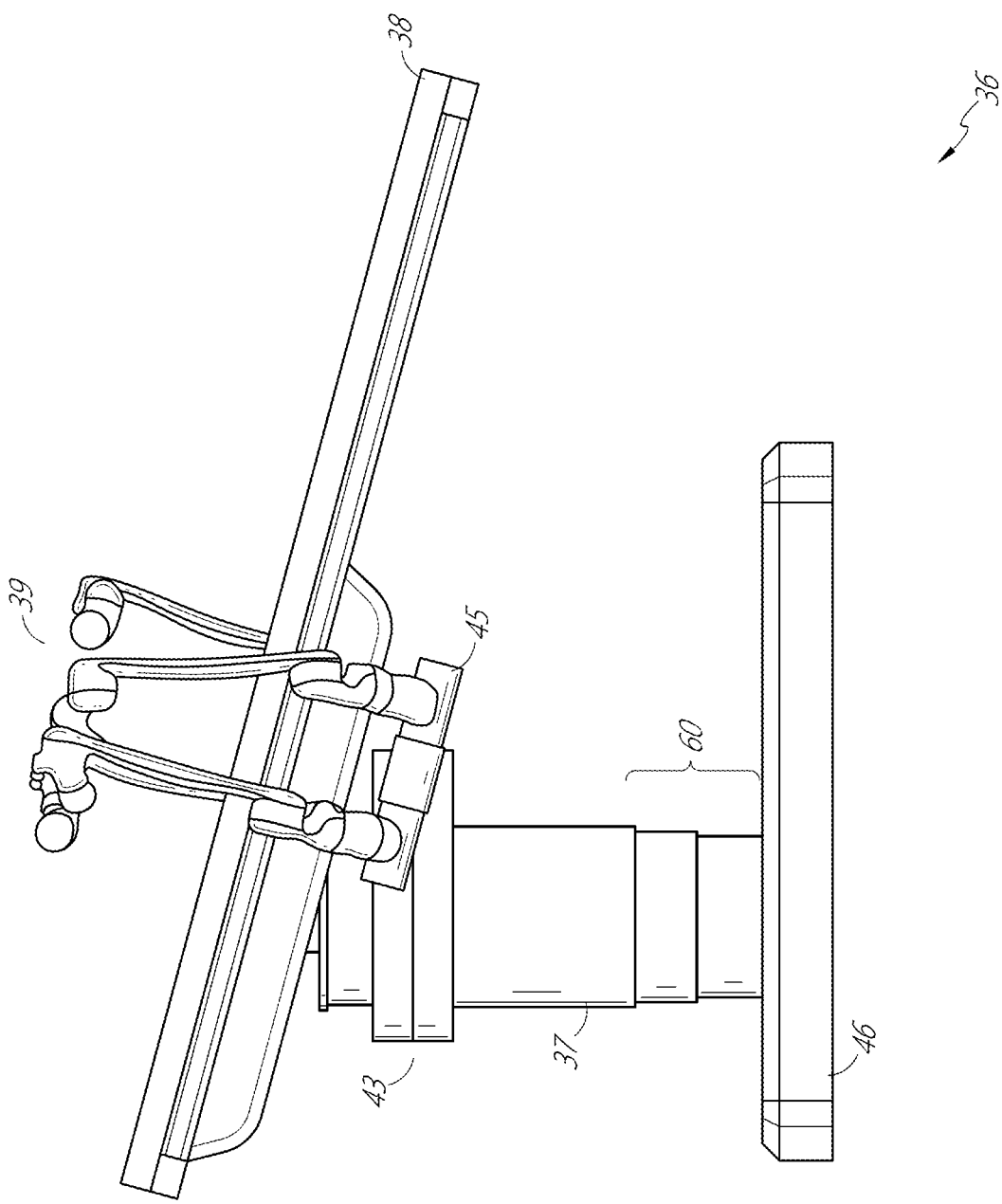
FIG. 10 illustrates an embodiment of the table-based robotic system of FIGS. 5-9 with pitch or tilt adjustment.

To accommodate laparoscopic procedures, the robotically enabled table system may also tilt the platform to a desired angle. FIG. 10 illustrates an embodiment of the robotically enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
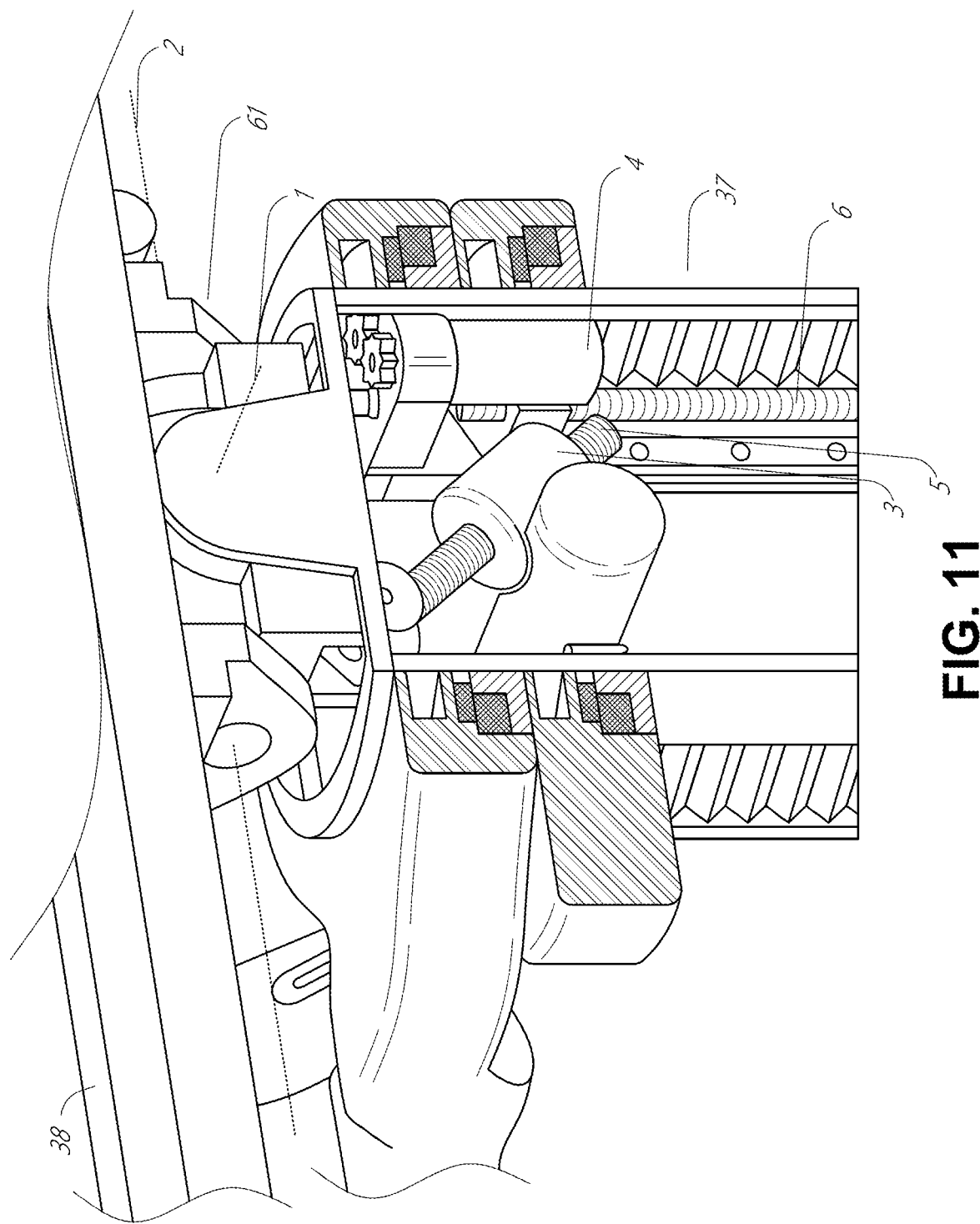
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
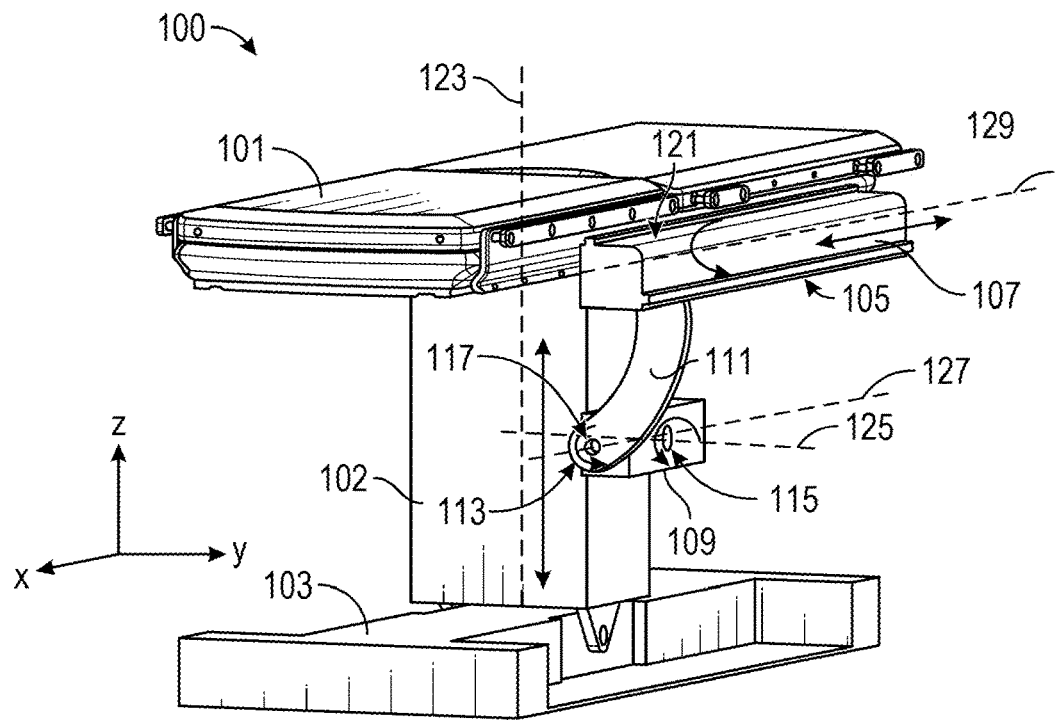
FIG. 12 illustrates an alternative embodiment of a table-based robotic system.
Figure 13:
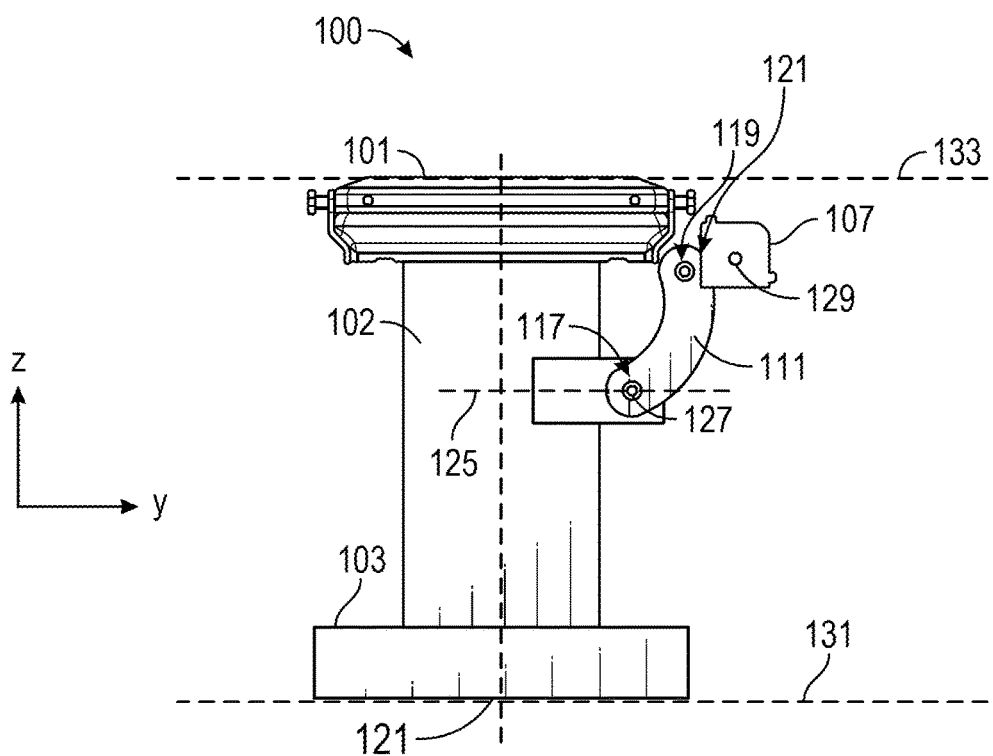
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
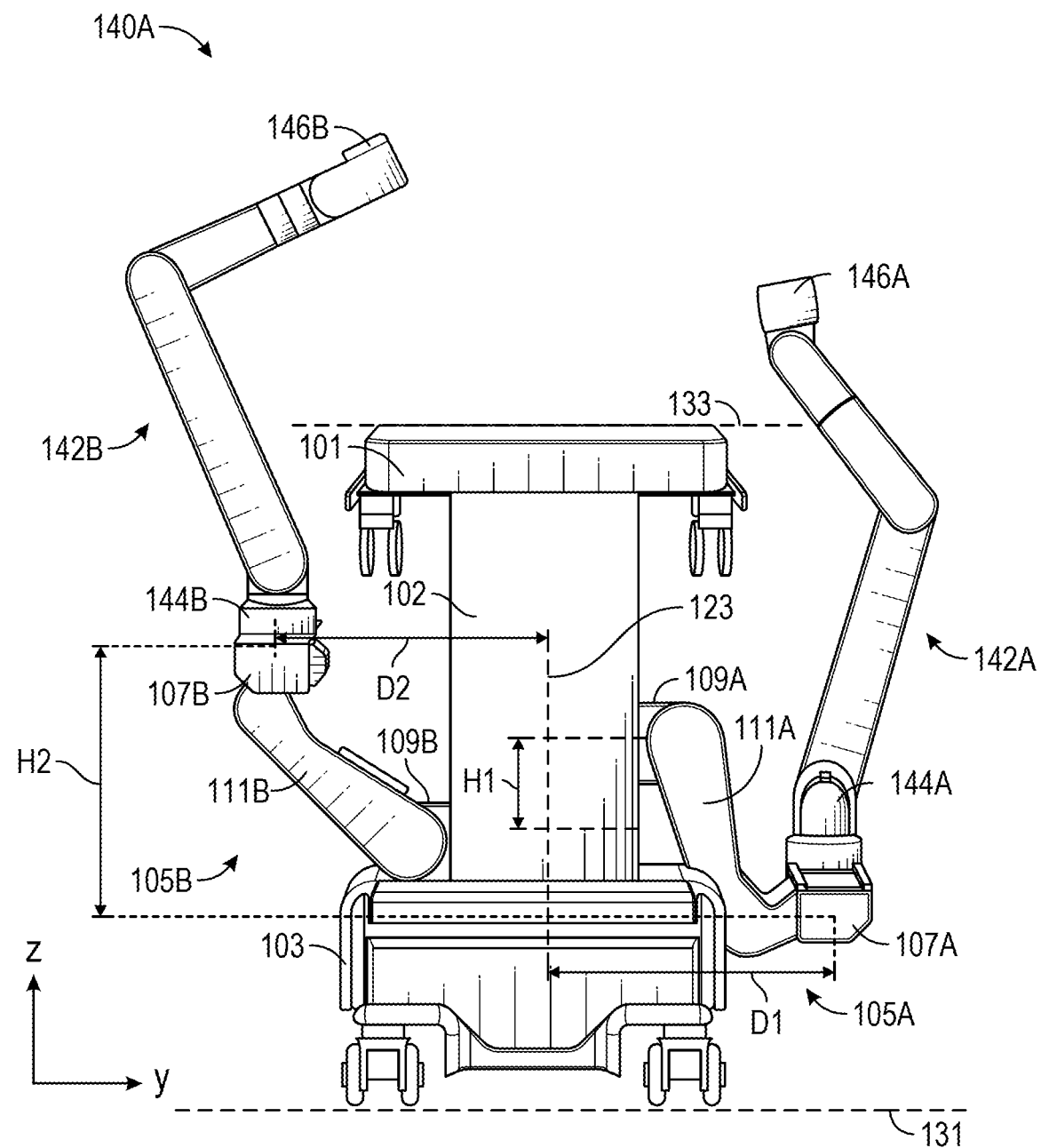
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
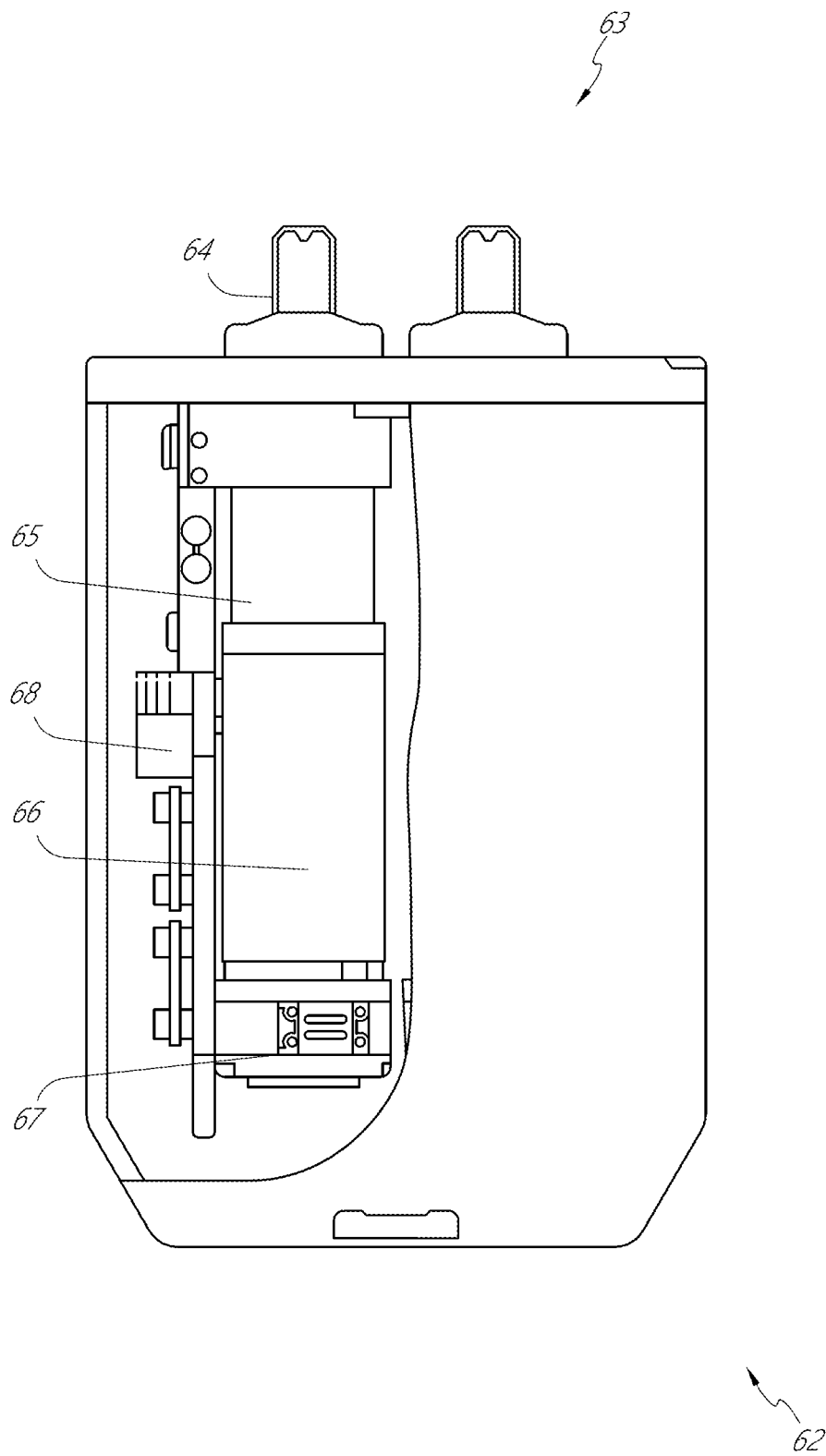
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
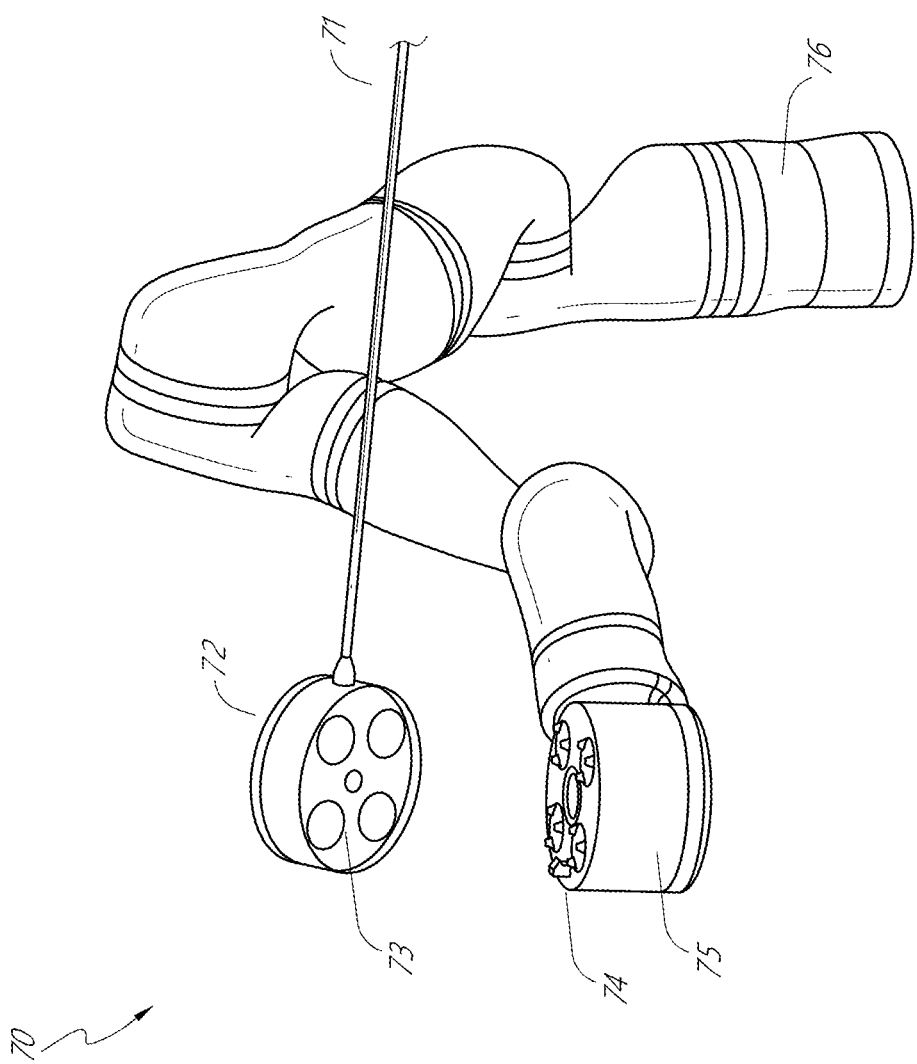
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
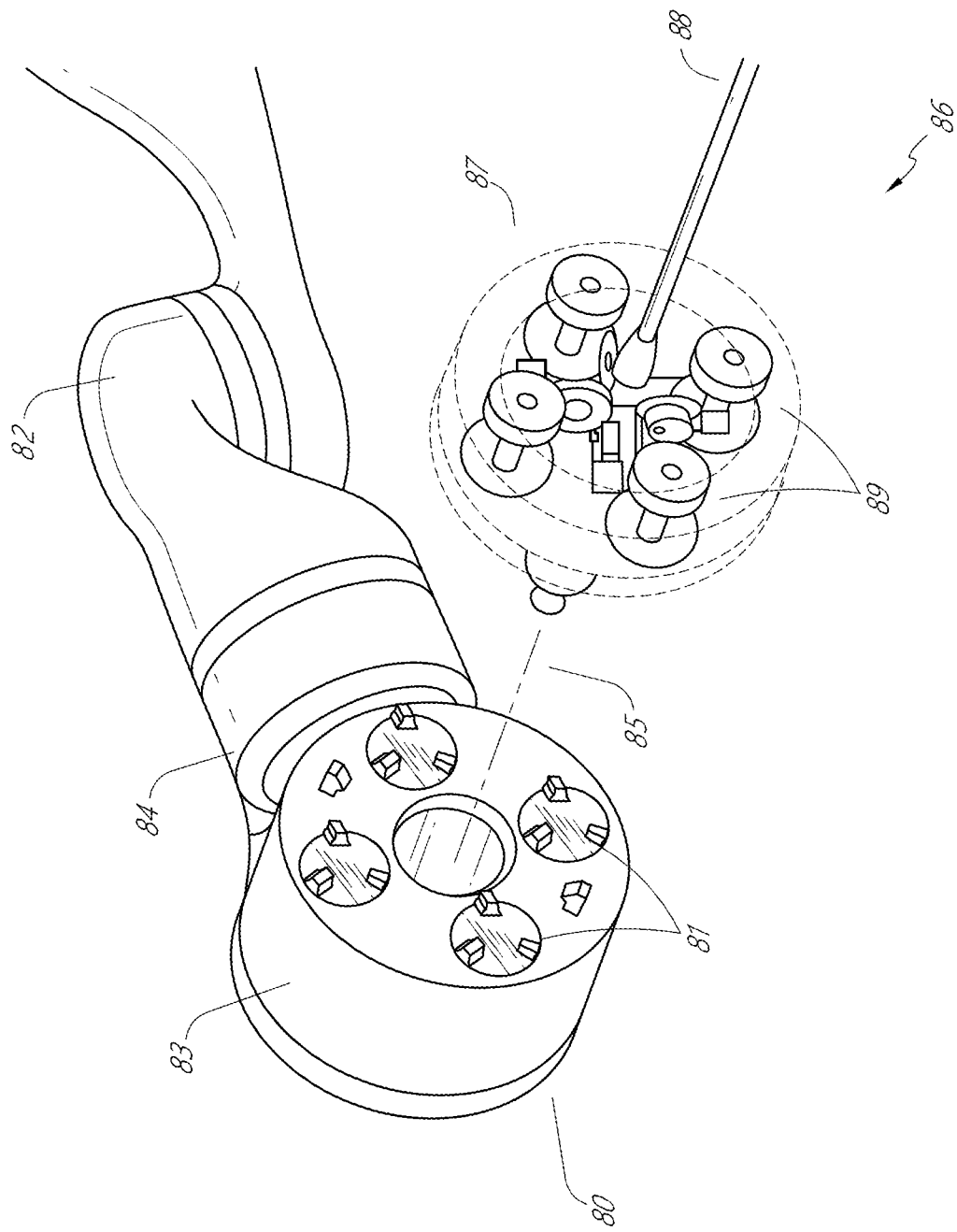
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
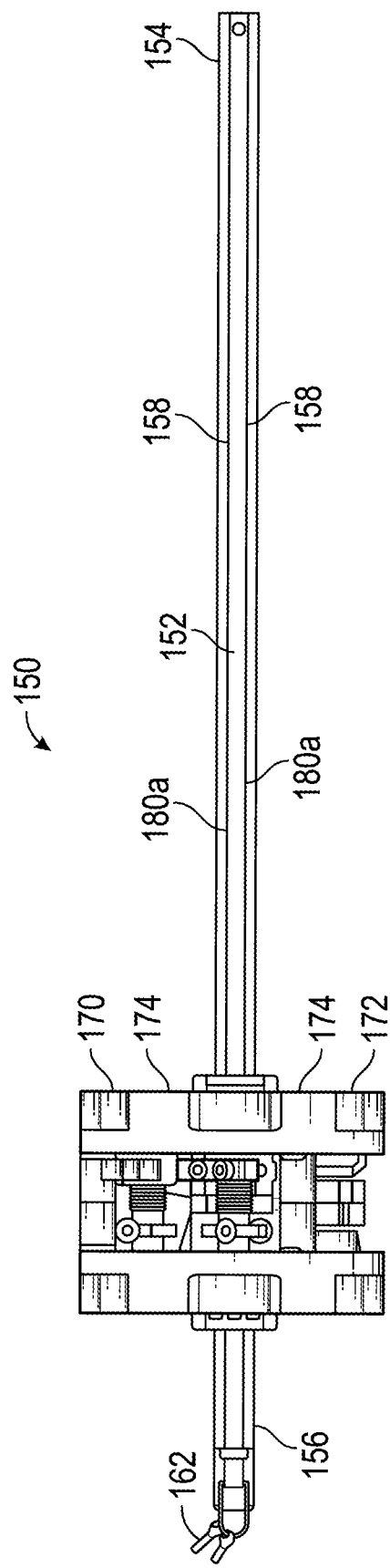
FIG. 18 illustrates an instrument having an instrument-based insertion architecture.

FIG. 18 illustrates an instrument having an instrument-based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver. In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
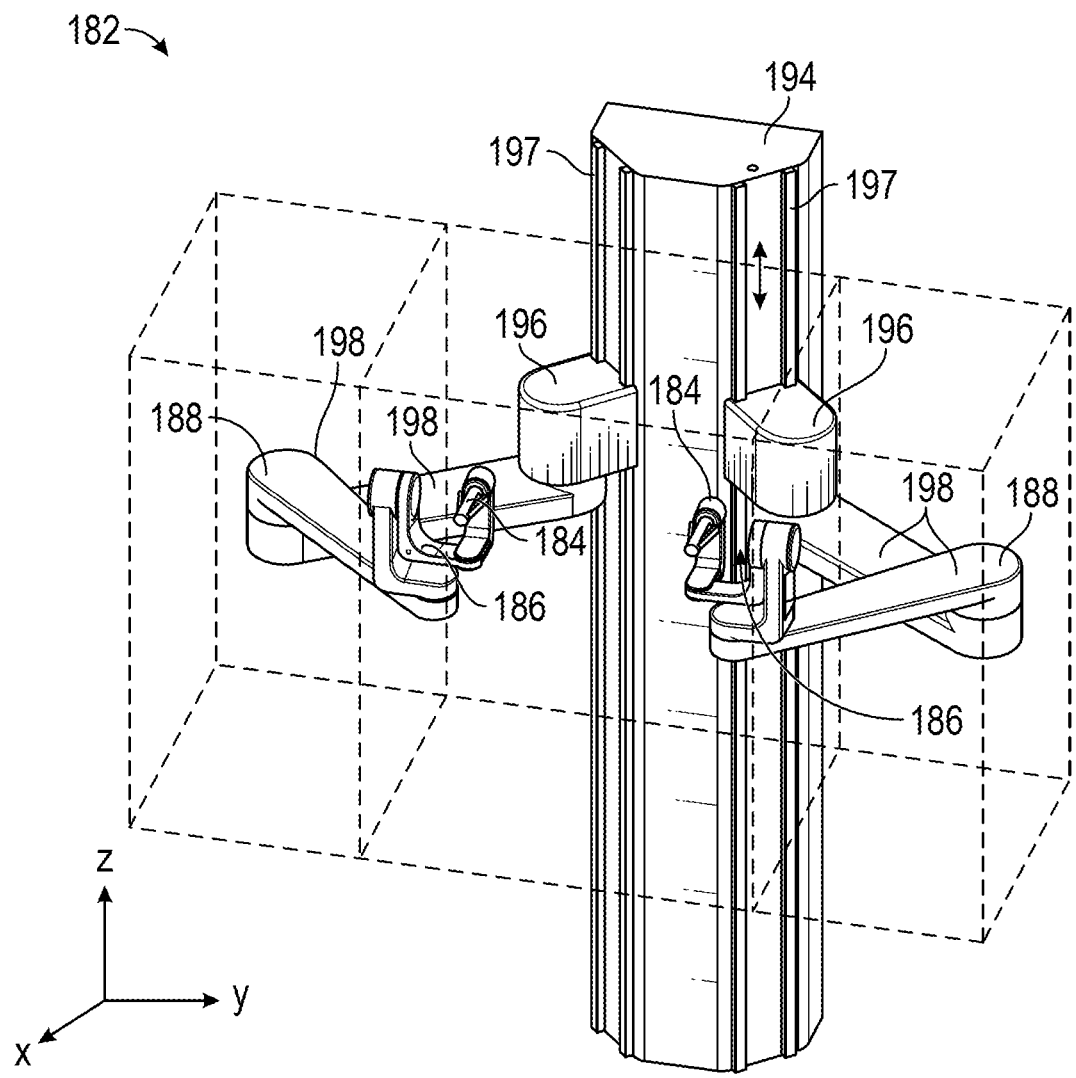
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
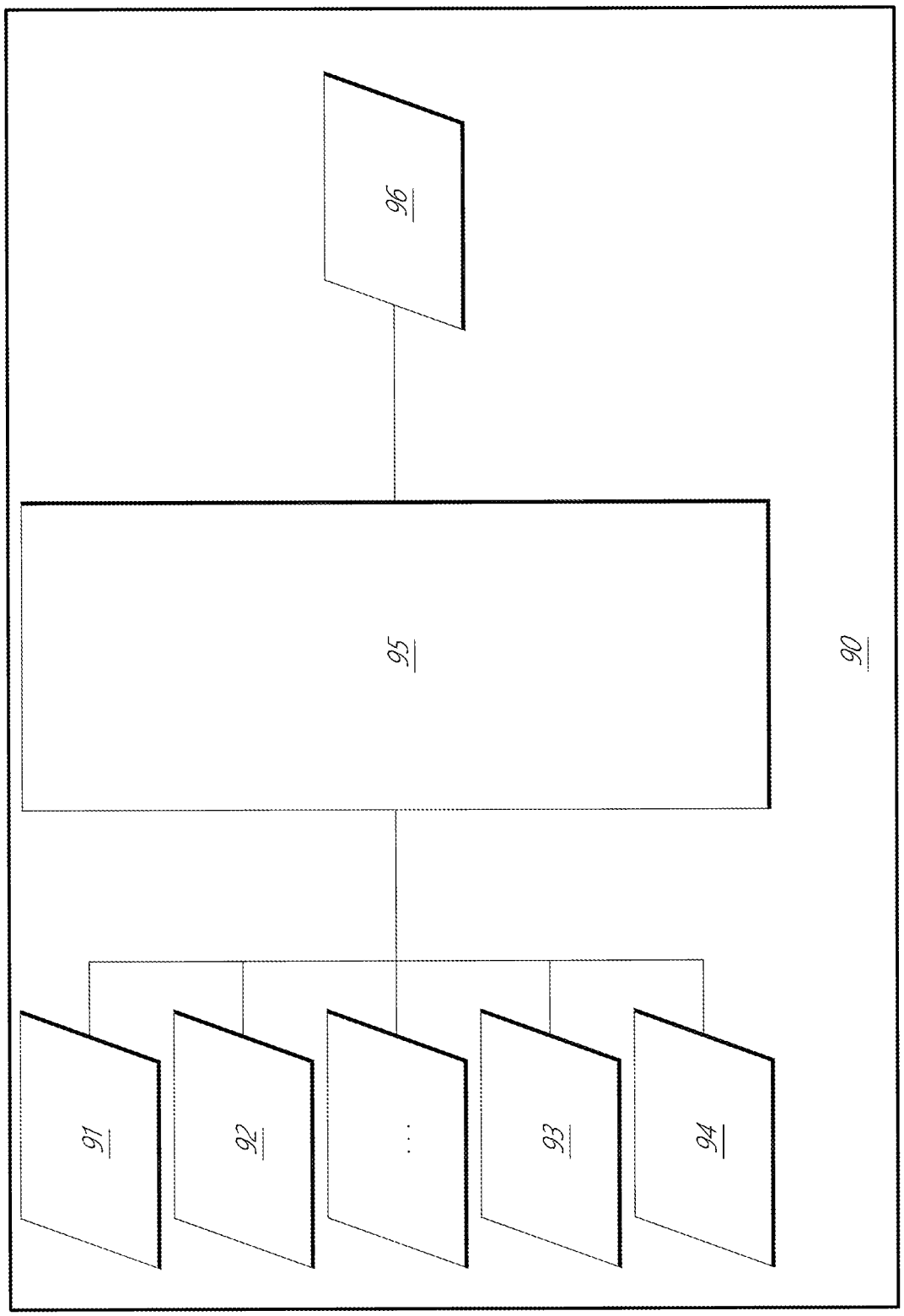
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Articulating Medical Instruments

This section relates to articulating medical instruments, as well as to related systems, techniques, and methods. In some embodiments, the articulating medical instruments can be used with robotically enabled medical systems, such as those described above with reference to FIGS. 1-20 and others. In some of the examples described in this section, the articulating medical instrument is described as a laparoscope that is configured for use during laparoscopic medical procedures. The principles of this disclosure, however, can be applied in other contexts and to other types of medical instruments, such as endoscopes, among others. For example, an articulating medical instrument as described in this application can be configured for use during any type of laparoscopic procedure, endoscopic procedure, open medical procedure, minimally invasive procedure or any other medical procedure.

In this application, the articulating medical instruments are described as "articulating" because the medical instruments include one or more flexible or bending portions as described below. In some embodiments, the one or more bending portions can comprise bending sections that are configured to allow articulation (e.g., bending, flexing, or otherwise changing the shape or pose) of the medical instrument. Articulation can facilitate the medical procedures in which the articulating medical instruments are used. For example, articulation can allow the medical instruments to be navigated through or reach a target anatomy. In some embodiments of this application, the articulating medical instruments are configured as inserting articulating medical instruments. The inserting articulating medical instruments are referred to as "inserting" because, in some embodiments, the instruments include an insertion architecture configured to insert and retract the medical instrument as described above with reference to FIG. 18 and further described below. In some embodiments, the insertion architecture of the inserting articulating medical instrument advantageously allows for insertion and retraction of the medical instrument without reliance on movement of a robotic arm to which the medical instrument is attached. In some embodiments, this can decrease the likelihood of robotic arm collisions during a procedure. Throughout this section, reference to a medical instrument is intended to refer to an "articulating medical instrument" and/or an "inserting articulating medical instrument" unless context dictates otherwise.

During laparoscopic procedures, there is often a need for visualization of an instrument workspace (e.g., a target anatomical region in which the procedure is to be performed) in order to perform the procedure effectively. Traditionally, laparoscopic procedures involve using a non-articulating laparoscope including a camera and at least two additional instruments that are able to move around and perform tasks while remaining under direct vision from the camera of the laparoscope. The laparoscope generally includes a non-articulating shaft (e.g., rigid) that is coupled to a robotic arm at a proximal end of the shaft. The robotic arm moves outside the patient's body to manipulate the position of the laparoscope and the orientation and view of the camera. For example, during the medical procedure the laparoscope is allowed to move through a cone of space above the patient to allow the operator to view the anatomy.

With an inserting articulating medical instrument as described herein, in some embodiments, the robotic arm may not require as much range of motion or reach outside of the patient's body due to the insertion architecture of the medical instrument. The insertion architecture allows an instrument handle or base of the medical instrument that is attached to the robotic arm to remain closely positioned to the patient's body, while an elongated shaft portion of the instrument can be inserted and retracted relative to the handle. Further, the bending section(s) of the medical instrument can allow for improved or enhanced views inside of the body that are not possible with a non-articulating laparoscope. For example, an articulating medical instrument can articulate through a range of positions providing a wider field of view. In some embodiments, the articulating medical instruments described herein can allow for more complicated procedures to be performed than with a non-articulating laparoscope. This may also allow the use of more medical instruments in the body because the articulating medical instrument does not sweep as large of a cone and take up as much space outside of the body.

Figure 21:
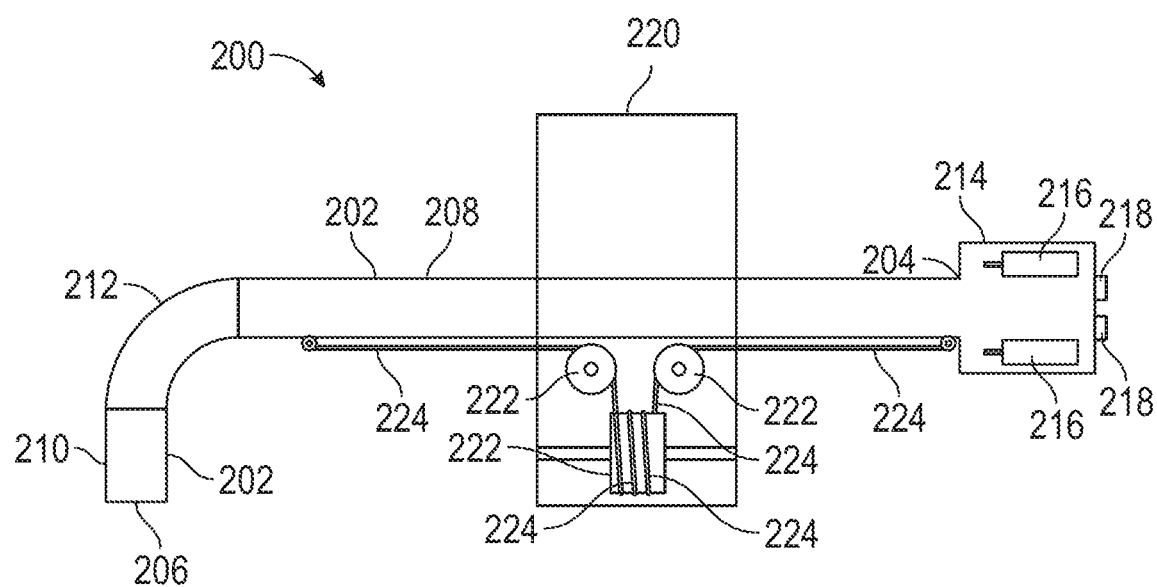
FIG. 21 illustrates an embodiment of an articulating medical instrument.
Figure 27B:
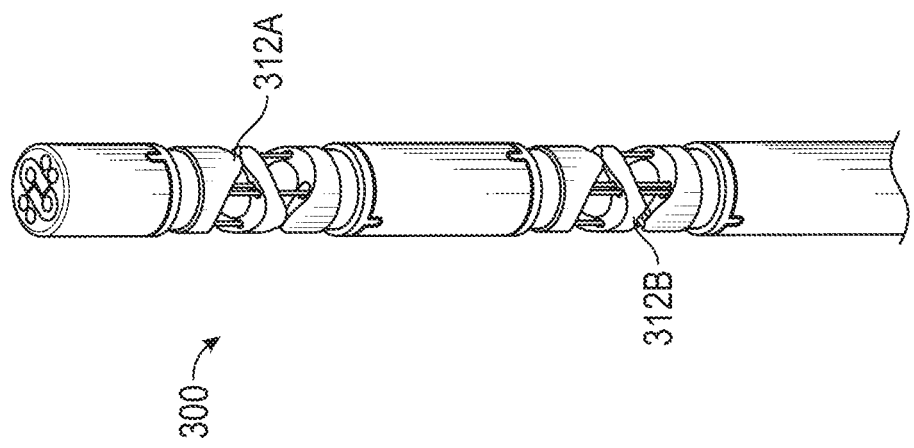
FIGS. 27A and 27B illustrate an embodiment of an articulating medical instrument that includes two bending sections.
Figure 27A:
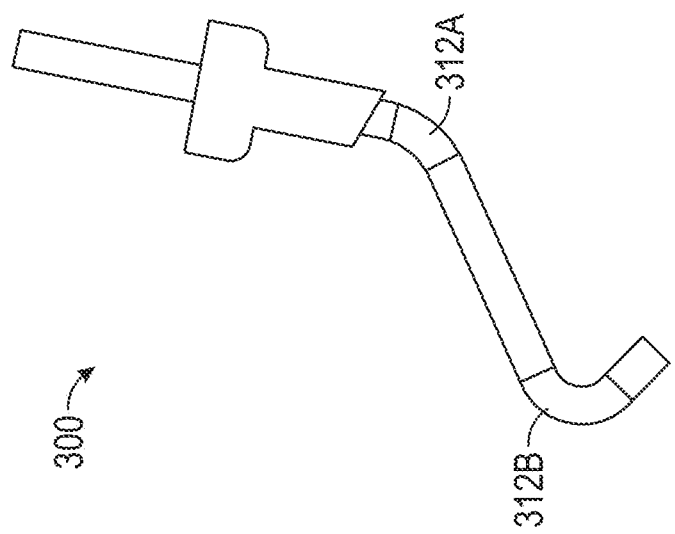

FIG. 21 illustrates a representation of an embodiment of an inserting articulating medical instrument 200. As illustrated, the medical instrument comprises an elongated shaft 202. The shaft 202 extends between a proximal end 204 and a distal end 206. The medical instrument 200 can be configured such that the distal end 206 can be inserted into a body of a patient during a medical procedure, while the proximal end 204 remains outside the body. In the illustrated embodiment, the shaft 202 comprises a first shaft section 208 and a second shaft section 210. The first shaft section 208 can extend between the proximal end 204 and an articulating or bending section 212 which will be described in more detail below. The second shaft section 210 can extend from the bending section 212 to the distal end 206. In some embodiments, each shaft section 208, 210 of the shaft 202 is substantially rigid, although this need not be the case in all embodiments. Although first and second shaft sections 208, 210 are illustrated in the embodiment of FIG. 21, in other embodiments, medical instruments can include more than two shaft sections. For example, FIGS. 27A and 27B, illustrate an example that includes three shaft sections. Further, although the embodiment of FIG. 21 includes only a single bending section 212, medical instruments can include more than one bending section. For example, FIGS. 27A and 27B, illustrate an example that includes two bending sections. In addition, although the embodiment of FIG. 21 shows a bending section that is less than half of the length of the shaft, in other embodiments, a much longer bending section can be provided, such as one that occupies greater than half of the length of the shaft or a majority of the length of the shaft.

The bending section 212 is configured to allow articulation or bending of the medical instrument 200. For example, the bending section 212 can allow for articulation between the first shaft section 208 and the second shaft section 210. The bending section 212 can be configured to allow for articulation or bending in one, two, or more degrees of freedom. For example, in some embodiments, the bending section 212 is configured to allow bending in at least two degrees of freedom (e.g., pitch and yaw directions). In some embodiments, the bending section 212 comprises a multi-link wrist. In some embodiments, the multi-link wrist comprises a snake wrist. Detailed embodiments of a snake wrist are described below with reference to FIGS. 23A and 23B and FIGS. 24A and 24B. In other embodiments, the bending section 212 may comprise other structures configured to allow bending or articulation, such as one or more hinged joints or pivot based bending sections. In some embodiments, the bending section may comprise a flexible material in addition to or in place of a mechanical joint. The use of the snake wrist design, as shown in FIGS. 23A-24B, can, in some instances be easier to control in a predictable manner than these other embodiments by having links with larger ranges of motion and direct control of each link.

In some embodiments, one or more tools or end effectors can be positioned at the distal end 206 of the elongated shaft 202. For example, in some embodiments, the distal end 206 can comprise a camera. Other types of tools or end effectors can also be positioned at the distal end 206, such as lights, graspers, cutters, clippers, cauterizers, etc. In some embodiments, the second shaft section 210 can be omitted, and the one or more tools or end effectors can be positioned at a distal end of the bending section 212.

At the proximal end 204 of the shaft 202, the medical instrument 200 may comprise an articulation handle 214. The articulation handle 214 may comprise one or more components that are configured to cause articulation of the bending section 212. For example, the articulation handle 113 may comprise one or more motors 216 configured to cause articulation of the bending section 212. In the illustrated embodiment, the articulation handle 214 includes two motors 216, although other numbers of motors 216 can be used in other embodiments. For example, the articulation handle 214 may comprise one, two, three, four, or more motors 216. The motors 216 can be electric motors. The motors 216 can be configured to cause rotation of one or more pulleys that can also be housed within the articulation handle 214. In some embodiments, pull wires wound on the pulleys are connected to the bending section 212. Rotation of the pulleys with the motors 216 can pull on or tension the pull wires to cause articulation of the bending section 212 as will be described in greater detail with reference to certain embodiments below.

In some embodiments, because the articulation handle 214 includes motors 216, the articulation handle 214 can advantageously be used to cause articulation of the bending section 212 regardless of whether the medical instrument 200 is attached to a robotic arm. This may, for example, allow the medical instrument 200 to be used manually in addition to robotically. In some embodiments, the medical instrument 200 may include one or more buttons or other inputs that can be used to control articulation of the bending section manually. In some embodiments, the medical instrument 200 includes connectors 218 for connecting various electronic components to the medical instrument 200. For example, in some embodiments, the connectors 218 can be configured to allow connection of power, light, and vision so that a light and camera on the distal end 206 can be used even when the medical instrument 200 is not connected to a robotic arm.

In addition to the articulation handle 214, in the illustrated embodiment, the medical instrument 200 also comprises an insertion handle 220. The insertion handle 220 can be configured to attach to an instrument drive mechanism (IDM) as described above. See for example, IDMs 146A, 146B described above with reference to FIG. 14. The IDMs can be positioned on robotic arms. In some embodiments, the IDMs include one or more motors configured to drive components of the articulation handle 214 as described above and below.

The insertion handle 220 can be configured to enable insertion or retraction of the shaft 202 relative to the insertion handle 220. For example, the insertion handle 220 can allow insertion or retraction of the shaft 202 along an insertion axis. This can advantageously reduce reliance on robotic arms to cause insertion or retraction of the instrument. For example, absent the insertion handle 220 and corresponding insertion architecture, a robotic arm may be required to move through a large range in order to insert or retract the device. In some embodiments, with the insertion handle 220, the insertion handle 220 and robotic arm can remain relatively stationary, while the insertion handle 220 drives insertion and retraction of the shaft 202. In some embodiments, the insertion axis is aligned with or parallel to a longitudinal axis of the first shaft section 208. The insertion handle 220 may provide an instrument-based insertion architecture for the medical instrument 200. An embodiment of an instrument-based insertion architecture is described above with reference to FIG. 18. The insertion handle 220 may comprise one or more pulleys 222 configured to drive one or more insertion cables 224. In some embodiments, the pulleys 222 are driven by the one or more motors of the IDM to which the insertion handle 220 is attached. As illustrated, a portion of the insertion cable 224 can extend along, on, or within the shaft 202. Driving the pulleys 222 can cause the insertion handle 220 to move along the shaft 202, thereby causing the shaft 202 to advance or retract relative to the insertion handle 220.

Thus, as shown in FIG. 21, in some embodiments, the medical instrument 200 can be configured for articulation and insertion. The medical instrument 200 advantageously includes two different handles—one for articulation and the other for insertion. Articulation may be driven by the motors 216 in the articulation handle 214 such that articulation is possible both when the medical instrument 200 is attached to an IDM and when the medical instrument 200 is not attached to an IDM. Insertion can de driven by one or more motors in the IDM to which the insertion handle 220 is attached. The motors in the IDM can drive the pulleys 222 in the insertion handle 220 which spool and unspool one or more insertion cables 224 to cause the shaft 202 to move relative to the insertion handle 220. In some embodiments, the insertion handle 220 and related features may be omitted such that the medical instrument 200 is not configured with an instrument-based insertion architecture.

As mentioned above, the medical instrument 200 may advantageously allow articulation even when the medical instrument is not coupled to an IDM and/or robotic arm. This can be beneficial because, in some instances, it may be desirable to use the medical instrument 200 manually before switching to robotic control. For example, during a first part of a procedure, the distal end 206 of the medical instrument 200 can be manually inserted into the patient before the medical instrument 200 is attached to an IDM or robotic arm. An operator can manually articulate the bending section 212 using one or more buttons or actuators on the medical instrument 200. In embodiments that include a camera, this may, for example, allow an operator to use the medical instrument 200 to look around under manual control before switching to robotic control. In contrast, under a classical articulating robotic instrument paradigm, articulation is driven by motors that get coupled to the instrument when the instrument is attached to the IDM or robotic arm. This means that, before the instrument is loaded, it has no way to control articulation.

In some embodiments, the medical instrument 200 advantageously includes both an articulation handle 214 and an insertion handle 220. The articulation handle 214 can include motors 216 for causing articulation. The insertion handle 220 can be motor-free and can be configured to engage with an IDM that drives insertion.

With the inclusion of the motors 216 in the articulation handle 214, the medical instrument 200 may advantageously allow for control over articulation even when the medical instrument 200 is not connected to an IDM. For example, in some embodiments, articulation is possible as soon as the connectors 218 are connected. If this power and control signaling is combined with the same connector as the video signal, an operator will have control of articulation whenever they have vision. In some embodiments, the medical instrument 200 may include batteries such that it can be used even without connecting the connectors 218.

In some embodiments, the shaft 202 of the medical instrument 200 could straighten and hold a straight position as soon as the medical instrument 200 gains power and until the medical instrument 200 is docked onto the IDM. As mentioned above, as an extension of this, articulation control buttons can be added that enable the operator to steer the articulation without the medical instrument 200 being docked to an IDM. In some embodiments, an absolute encoder, such as, e.g., magnetic encoder(s), may be included on the drive spool(s) in addition to any encoder that may be on the motor rotor shaft related to commutation and/or servos, such that the position of the bending section 212 is known as soon as the medical instrument 200 receives power.

In some embodiments, the medical instrument 200 is capable of providing an instinctive and manageable driving experience for the operator, compared to other manually articulated laparoscopes or endoscopes. Also, the bending section 212, which may comprise a snake wrist, may provide a more deterministic driving experience and more stable articulation than other manual devices.

These and other features and advantages of the articulating (and inserting articulating) medical instruments will now be described with reference to the detailed embodiments of FIGS. 22A-28. These embodiments are provided by way of example and are intended to illustrate principles of this disclosure without limiting the disclosure.

A. Example Articulation Handle

The medical instrument 200 is unique in that the articulation handle 214 can include motors 216 that are configured to cause articulation of the medical instrument. In contrast, in predicate devices, motors for articulation are generally located in an instrument drive mechanism or the robotic arm itself. By having motors 216 in the articulation handle 214, the medical instrument 200 can advantageously provide the freedom for articulating the medical instrument 200 even when detached from a robotic arm. For example, the articulation handle 214 could be detached from the robotic arm and commanded to articulate via one or more buttons as part of a manual procedure. Further, with the motors 216 housed in the articulation handle 214, the medical instrument 200 can comprise a sealed architecture. In some embodiments, a sealed architecture can facilitate sterilization. In some embodiments, this can reduce the total number of components in the robotic system that need to be sealed. For example, in some embodiments, because the medical instrument 200 comprises a sealed architecture, robotic arm rotary joints do not need to be sealed.

Figure 22A:
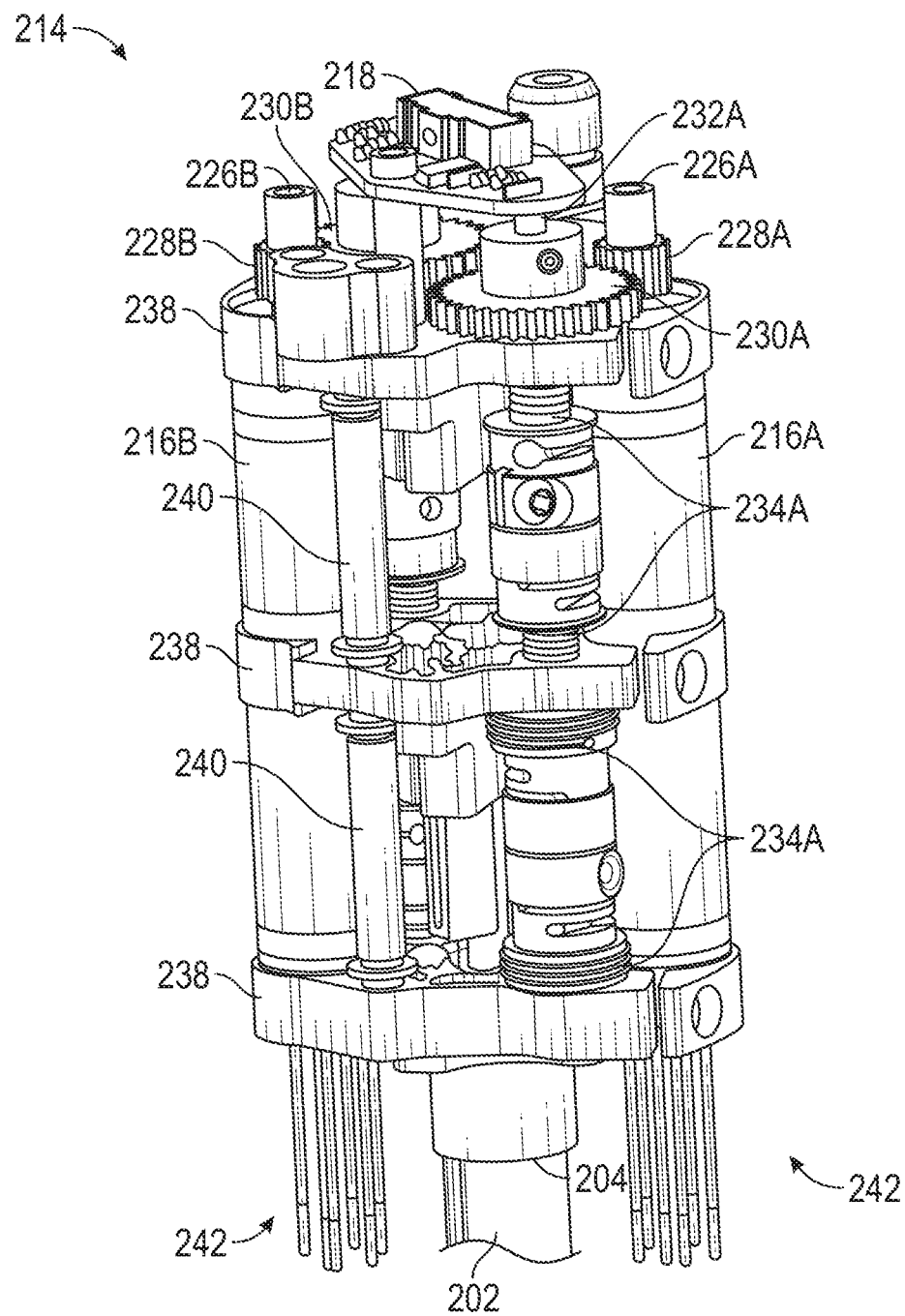
FIGS. 22A-22C illustrate perspective views of some internal components of an articulation handle for an articulating medical instrument, according to an embodiment.

FIG. 22A is an isometric view of internal components of an embodiment of the articulation handle 214. In FIG. 22A, a housing of the articulation handle 214 has been removed so that the internal components can be seen. In the illustrated embodiment, the articulation handle 214 includes a first motor 216A and a second motor 216B for driving articulation (referred to collectively as the motors 216). In some embodiments, a gear, such as a planetary gearhead, can be combined or installed on the first motor 216A and/or second motor 216B. Each of the motors 216 can include a drive shaft 226A, 226B, respectively (referred to collectively as the drive shafts 226). In the illustrated embodiment, motor gears 228A, 228B (referred to collectively as the motor gears 228) are mounted on each drive shaft 226A, 226B. The motors 216 are configured to cause rotation of the drive shafts 226 to cause rotation of the motor gears 228. In some embodiments, each motor 216 can be operated independently such that each motor gear 228 can be rotated individually.

Figure 22B:
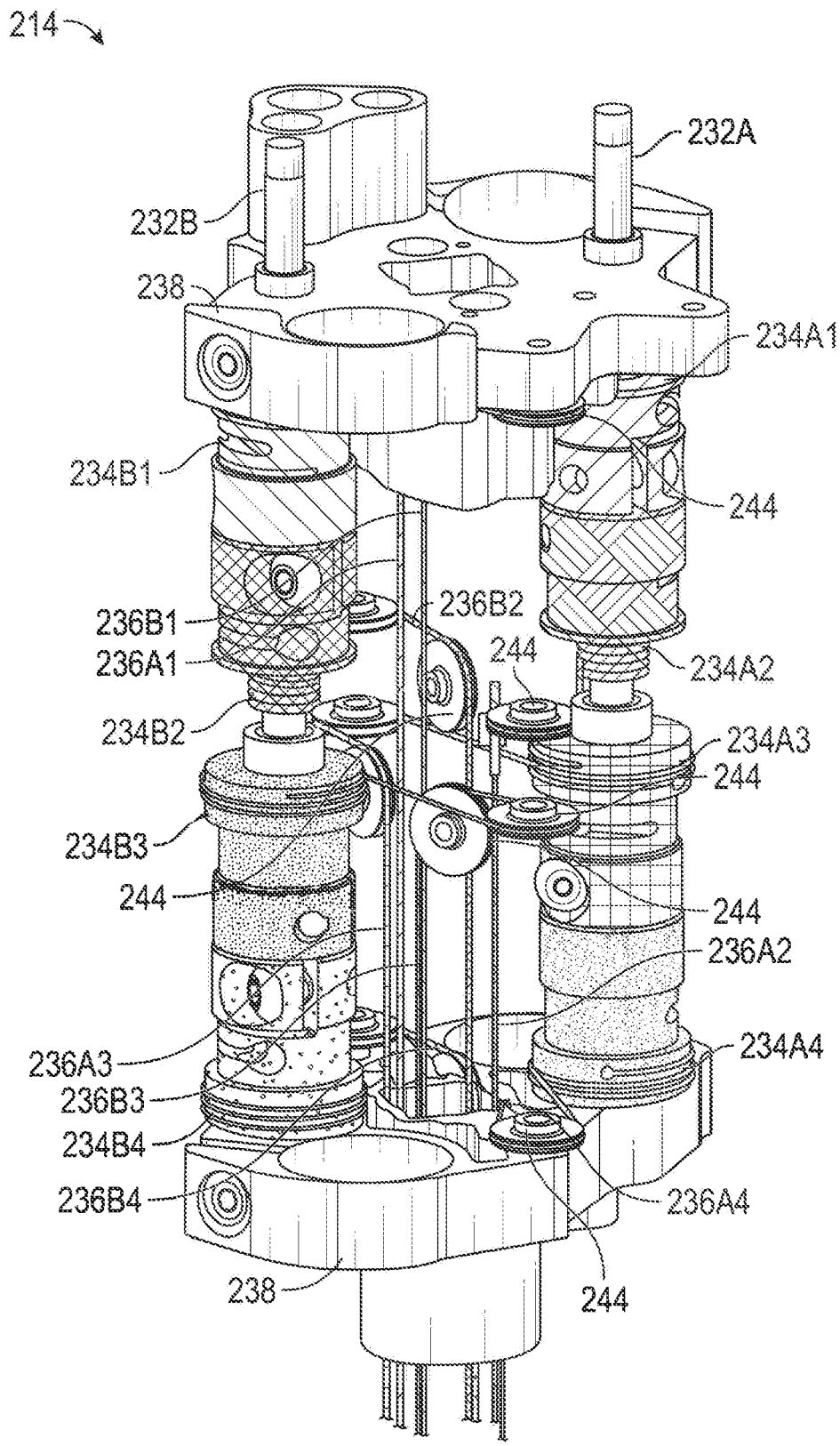

In the illustrated embodiment, each motor gear 228 is operatively engaged with a shaft gear 230A, 230B (referred to collectively as the shaft gears 230). Each shaft gear 230 can be mounted on a respective output shaft 232A, 232B (referred to collectively as the output shafts 232). The output shaft 232B is not visible in FIG. 22A, but is shown in FIG. 22B. Thus, in the illustrated embodiment, rotation of the motors 216 is transmitted to the output shafts 232 through the motor gears 228 and shaft gears 230. Other systems and configurations for causing rotation of the output shafts 232 are also possible.

In the illustrated embodiment, helical capstans or pulleys 234 are mounted on the output shafts 232. In FIG. 22A, only the pulleys 234A that are mounted on the first output shaft 232A are easily visible. In the illustrated example, four pulleys 234A are shown. Four pulleys 234B (shown in FIGS. 22B and 22C) can also be included on the second output shaft 232B. These eight pulleys 234 are specifically identified as pulleys 234A1-234A4 and 234B1-234B4 in FIGS. 22A-22C, which are described in greater detail below. In general, the pulleys 234A that are mounted on the output shaft 232A all rotate together, and the pulleys 234B that are mounted on the output shaft 232B all rotate together. Each pulley 234 can be associated with a pull wire 236 (not shown in FIG. 22A, but illustrated and specifically identified as pull wires 236A1-236A4 and 236B1-236B4 in FIGS. 22A-24B, which are described below). For example, the pull wires 236 can be wound on the pulleys 234. Thus, for the illustrated embodiment, each motor 216 can be actuated to control four pull wires 236 at the same time. Further, in some embodiments, each motor 216 can be driven in both clockwise and counterclockwise direction to pay in and out the pull wires 236.

Figure 22C:
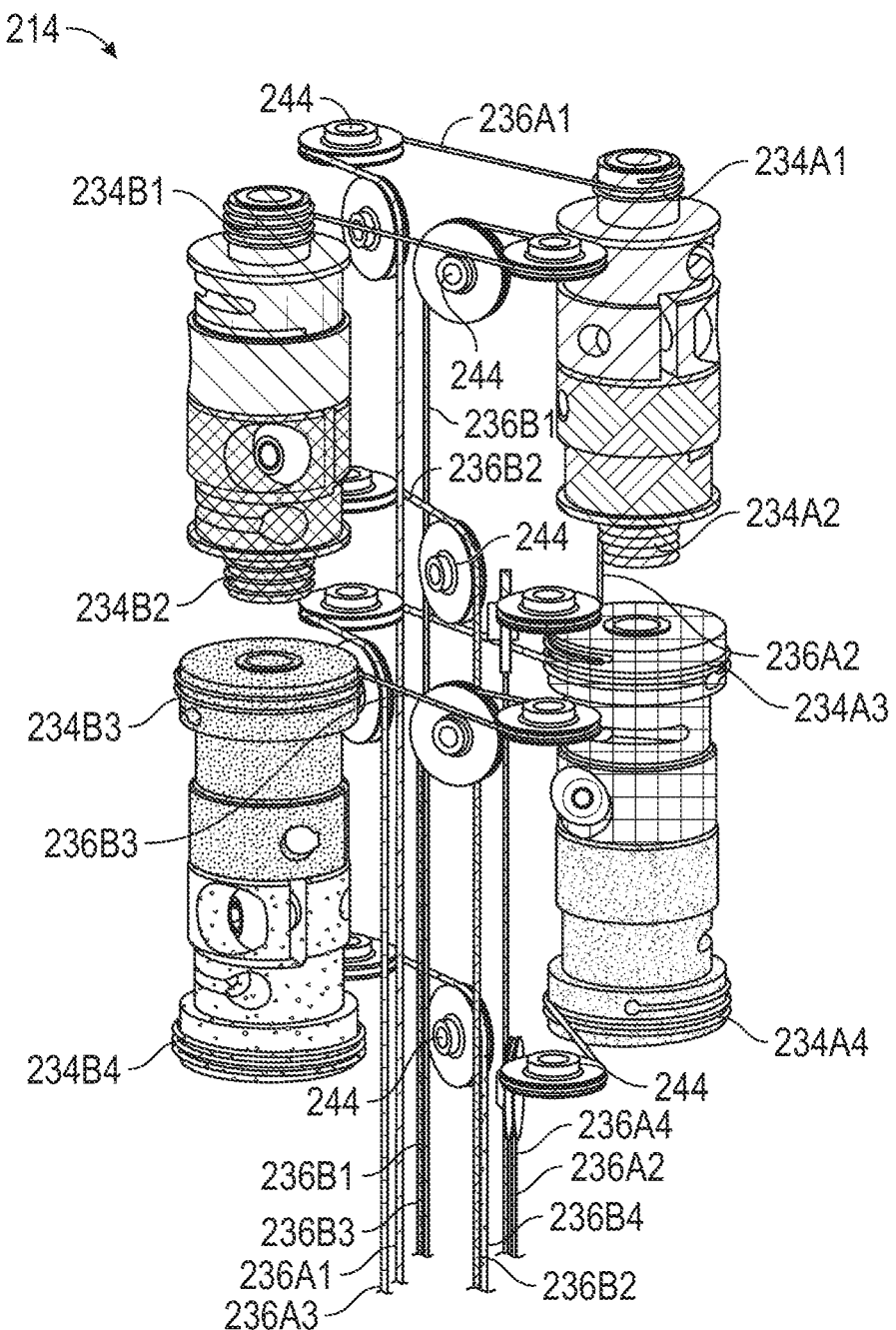

With continued reference to FIG. 22A, the articulation handle 214 can also comprise brackets 238. The brackets 238 can be configured to support and hold the motors 216 and output shafts 232. The brackets 238 can include one or more openings that allow the pull wires 236 to pass therethrough. In the illustrated embodiments, the brackets 238 are separated and supported by clamping onto motors 216. One or more supports or spacers 240 (e.g., for redirect pulleys 244 as shown in FIGS. 22B and 22C) can extend between the brackets 238. FIG. 22A also illustrates leads 242 for the motors 216. The leads 242 can be connected to power and motor controllers that drive the motors 216. Further, FIG. 22A illustrates an example of the connector 218, which as described above can be used to make various connections (e.g., power, light, vision, etc.) between the medical instrument 200 and a robotic medical system. As illustrated, the proximal end 204 of the shaft 202 can be connected to the articulation handle 214. For example, the proximal end 204 of the shaft 202 can be connected to one of the brackets 238. In some embodiments, the shaft 202 is rigidly and fixedly attached to the articulation handle 214.

FIGS. 22B and 22C further illustrate the embodiment of the articulation handle 214 shown in FIG. 22A. In FIG. 22B, the housing, motors 216, supports 240, and certain brackets 238 have been removed. In FIG. 22B, the output shafts 232 and remaining brackets 238 have also been removed. In FIG. 22C, additional components of the articulation handle 214 have been removed to better illustrate the pulleys 234, pull wires 236, and certain other features of the articulation handle 214. Further, in FIGS. 22B and 22C, the pulleys 234 and corresponding pull wires 236 have been illustrated with different hatching patterns for clarity. That is, as illustrated, each pull wire 236 is illustrated with the same hatching pattern as the associated pulley 234.

As illustrated in FIG. 22B, the first pulley 234A1, the second pulley 234A2, the third pulley 234A3, and the fourth pulley 234A4 are mounted on the first output shaft 232A. Similarly, the first pulley 234B1, the second pulley 234B2, the third pulley 234B3, and the fourth pulley 234B4 are mounted on the first output shaft 232A.

Each pulley 234 is associated with one pull wire 236. In the illustrated example, the first pull wire 236A1 is associated with the first pulley 234A1, the second pull wire 236A2 is associated with the second pulley 234A2, the third pull wire 236A3 is associated with the third pulley 234A3, and the fourth pull wire 236A4 is associated with the fourth pulley 234A4 of the first output shaft 232A. Similarly, the first pull wire 236B1 is associated with the first pulley 234B1, the second pull wire 236B2 is associated with the second pulley 234B2, the third pull wire 236B3 is associated with the third pulley 234B3, and the fourth pull wire 236B4 is associated with the fourth pulley 234B4 of the first output shaft 232B. In some embodiments, a pull wire 236 being associated with pulley 234 means that the pull wire 236 is wound on the pulley 234.

For example, as illustrated, in some embodiments, each pull wire 236 is wound on the corresponding pulley 236. In some embodiments, the first and third pull wires 236A1, 236A3 of the first output shaft 232A are wrapped on the corresponding first and third pulleys 234A1, 234A3 in a first direction (e.g., counterclockwise), and the second and fourth pull wires 236A2, 236A4 of the first output shaft 232A are wrapped on the corresponding second and fourth pulleys 234A2, 234A4 in a second direction (e.g., clockwise) that is opposite the first direction. This configuration may allow the first and third pulleys 234A1, 234A3 to spool the first and third pull wires 236A1, 236A3, while the second and fourth pulleys 234A2, 234A4 unspool the second and fourth pull wires 236A2, 236A4 as the first output shaft 232A is rotated in the first direction. Similarly, this configuration allows the first and third pulleys 234A1, 234A3 to unspool the first and third pull wires 236A1, 236A3, while the second and fourth pulleys 234A2, 234A4 spool the second and fourth pull wires 236A2, 236A4 as the first output shaft 232A is rotated in the second direction.

In some embodiments, the first and third pull wires 236B1, 236B3 of the second output shaft 232B are wrapped on the corresponding first and third pulleys 234B1, 234B3 in a first direction (e.g., counterclockwise), and the second and fourth pull wires 236B2, 236B4 of the second output shaft 232B are wrapped on the corresponding second and fourth pulleys 234B2, 234B4 in a second direction (e.g., clockwise) that is opposite the first direction. This configuration may allow the first and third pulleys 234B1, 234B3 to spool the first and third pull wires 236B1, 236B3, while the second and fourth pulleys 234B2, 234B4 unspool the second and fourth pull wires 236B2, 236B4 as the second output shaft 232B is rotated in the first direction. Similarly, this configuration allows the first and third pulleys 234B1, 234B3 to unspool the first and third pull wires 236B1, 236B3, while the second and fourth pulleys 234B2, 234B4 spool the second and fourth pull wires 236B2, 236B4 as the second output shaft 232B is rotated in the second direction. Those of ordinary skill in the art will appreciate the pull wires 236 can be wound on the pulleys 234 in other configurations in other embodiments.

As illustrated in FIG. 22B, the insertion handle 220 can include a plurality of idler pulleys 244 configured to reroute the pull wires 236 from the pulleys 234 down the shaft 202. In the illustrated embodiment, two idler pulleys 244 are used for each pull wire 236. In other embodiments, other numbers of idler pulleys 244 can be used. For clarity, not every idler pulley 244 has been labeled in FIG. 22B. In some embodiments, the idler pulleys 244 are supported by the brackets 238.

FIG. 22C includes only the pulleys 234, pull wires 236, and idler pulleys 244 of the illustrated embodiment of the articulation handle 214 to further illustrate how the pull wires 236 can be routed. For clarity, not all idler pulleys 244 are labeled. Cross hatching in FIG. 22C of the pulleys 234 and pull wires 236 is consistent with FIG. 22B.

For the embodiment of the articulation handle 214 illustrated in FIGS. 22A-22C, two motors 216 drive two output shafts 232. Each output shaft 232 is associated with four pulleys 234 and four pull wires 236. The motors 216 can be used to rotate the pulleys 234 to spool and unspool the pull wires 236. As described below, the pull wires 236 are also associated with the bending section 212. Spooling and unspooling the pull wires 236 can be used to control articulation of the bending section 212. Other embodiments of the articulation handle 214 are also possible.

B. Example Bending Section

Figure 23A:
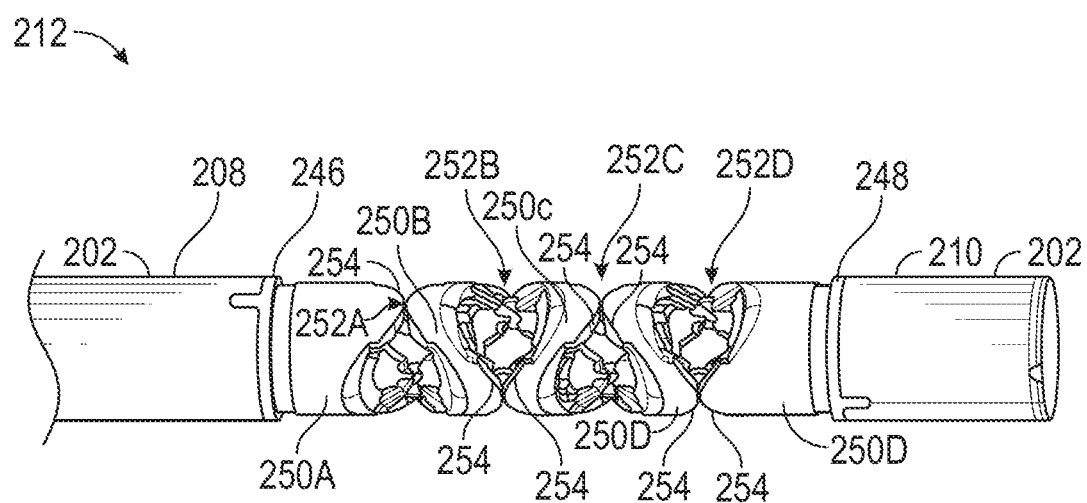
FIGS. 23A and 23B, are perspective and top views, respectively, of an embodiment of a bending section of an articulating medical instrument.
Figure 23B:
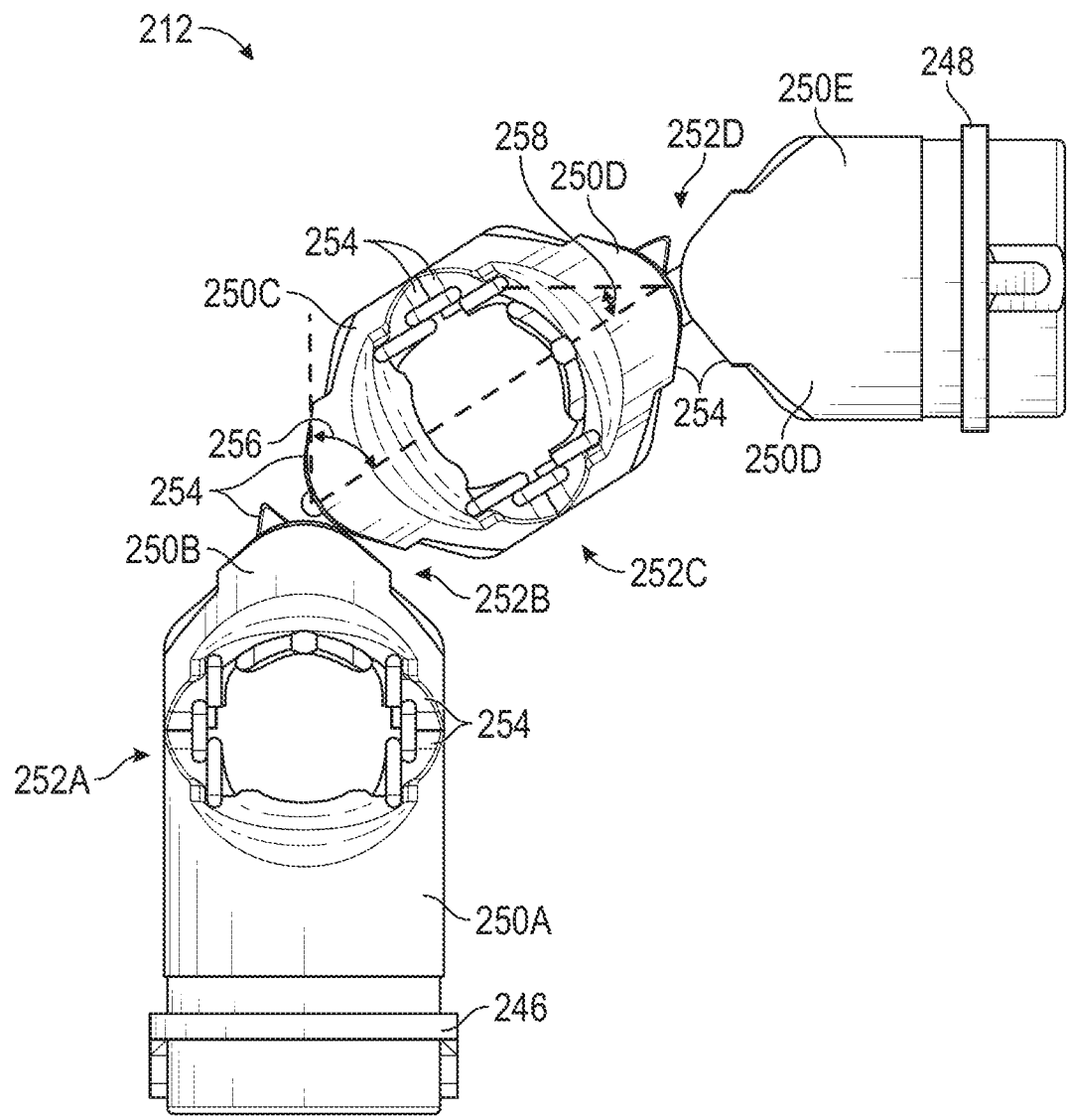

FIGS. 23A and 23B illustrate example bending sections 212 that are configured as snake wrists. FIG. 23A is a perspective view of the bending section 212 in an unarticulated (e.g., straight configuration), and FIG. 23B is a top view of the bending section 212 illustrated in an articulated configuration. As will be described in greater detail below with reference to FIGS. 24A and 24B, the bending section 212 configured as a snake wrist can be articulated using the pull wires 236 described above with reference to FIGS. 22A-22C. First, however, the structure of the illustrated snake wrist bending section 212 will be described.

As illustrated in FIG. 23A, the bending section 212 can be positioned between the first section 208 and the second section 210 of the shaft 202. As illustrated, a proximal end 246 of the bending section 212 is connected to the first section 208, and a distal end 248 of the bending section 212 is connected to the second section 210. As described below, the bending section 212 is articulable to allow bending between the first section 208 and the second section 210 of the shaft 202. In some embodiments, the first and second sections 208, 210 are rigid, such that any significant bending can only occur at the bending section 212.

As shown, the bending section 212, configured as a snake wrist as in the illustrated embodiment, can comprise a series of links 250. In the illustrated embodiment, the links 250 comprise a first link 250A, a second link 250B, a third link 250C, a fourth link 250D, and a fifth link 250E arranged serially between the proximal end 246 and the distal end 248. In the illustrated embodiment, a joint 252 is formed between each pair of links 250. As illustrated, four joints 252 are formed between the five links 250. Specifically, in the illustrated embodiment, a first joint 252A is formed between the first link 250A and the second link 250B, a second joint 252B is formed between the second link 250B and the third link 250C, a third joint 252C is formed between the third link 250C and the fourth link 250D, and a fourth joint 252D is formed between the fourth link 250D and the fifth link 250E.

In the illustrated embodiment, the joints 252 are configured as rolling joints formed between curved contact surfaces 254 of adjacent links 250. As illustrated, the curved contact surfaces 254 can be convex.

As illustrated in FIG. 23A, the second link 250B, the third link 250C, and the fourth link 250D include a curved surface 254 on each side thereof. In some embodiments, the one or more curved surfaces 254 can serve as rolling pivots having associated cycloid teeth that provide geared constraints for the rolling pivots. In the illustrated embodiment, for each of the second link 250B, the third link 250C, and the fourth link 250D, the curved surface 254 on one side is oriented at 90 degrees from the curved surface 254 on the opposite side. In some embodiments, this configuration allows each successive joint 252 to be formed at 90 degrees from the previous joint 252. Stated another way, this configuration allows each successive joint 252 to permit articulation in a direction that is 90 degrees from the direction of articulation of the previous joint 252.

For example, in the illustrated embodiment, the first joint 252A is configured to permit articulation in a first degree of freedom (for example, pitch). The second joint 252B is configured to permit articulation in a second degree of freedom (for example, yaw) that is oriented at 90 degrees from the first degree of freedom. The third joint 252C is configured to permit articulation in the first degree of freedom (in this example, pitch), and the fourth joint 252D is configured to permit articulation in the second degree of freedom (in this example, yaw). Thus, the bending section 212 is configured to allow articulation in two degrees of freedom, which can be pitch and yaw, for example. Stated another way, the first joint 252A can be a proximal pitch joint allowing for an angle of proximal pitch articulation, the second joint 252B can be a proximal yaw joint allowing for an angle of proximal yaw articulation, the third joint 252C can be distal pitch joint allowing for an angle of distal pitch articulation, and the fourth joint 252D can be a distal yaw joint allowing for an angle of distal yaw articulation.

In some embodiments, including more than one joint 252 in each degree of freedom can increase the range of motion of the bending section 212 in that degree of freedom. For example, the top view of FIG. 23B illustrates that articulation of each joint 252 associated with a degree of freedom can be cumulative. For example, as illustrated, the second joint 252B is articulated 45 degrees (see the illustrated angle 256), and the fourth joint 252D is articulated 45 degrees (see the illustrated angle 258), for a total articulation of the bending section 212 of 90 degrees in one degree of freedom. In some embodiments, the angle of the second joint 252B and the fourth joint 252D is substantially equal. In some embodiments, the angle of the second joint 252B and the fourth joint 252D may differ slightly, such as less than 3 degrees, or less than 5 degrees.

As will be discussed in greater detail below, in some embodiments, it can be advantageous that the angle of proximal pitch articulation be substantially equal to the angle of distal pitch articulation. That is, for a commanded angle of articulation in the pitch direction, it may be desirable for each of the angle of proximal pitch articulation and the angle of distal pitch to be about half the commanded angle of articulation in the pitch direction. Similarly, it can be advantageous for the angle of proximal yaw articulation to be substantially equal to the angle of distal yaw articulation. That is, for a commanded angle of articulation in the yaw direction, it may be desirable for each of the angle of proximal yaw articulation and the angle of distal yaw to be about half the commanded angle of articulation in the yaw direction. For example, suppose a clinician desires a pitch articulation of 90 degrees, then it may be desirable to have a proximal pitch angle of 45 degrees and a distal pitch angle of 45 degrees. Likewise, if a clinician desires a yaw articulation of 70 degrees, then it may be desirable to have a proximal yaw angle of 35 degrees and a distal yaw angle of 35 degrees. By keeping the articulation angles equal or substantially equal, this may help reduce the likelihood that one joint 252 will bottom out and degrade before the other, thereby maximizing the motion and lifespan of the bending section 212. Features of the medical instrument 200 that allow for this are described in greater detail below.

FIG. 23B illustrates the proximal angle of articulation 256 and the distal angle of articulation 258 of either the pitch or yaw joints during articulation of the bending section 212, which, as just noted, may advantageously be kept substantially equal. In some embodiments, the articulation angle can be defined as the angle that a link 250 articulates relative to a central axis (or midline or neutral axis) between adjacent links 250 when the links 250 are positioned so as to be straight relative to one another.

As will be described in greater detail below, the medical instrument 200 can include two unique cooperating features that can help to keep the proximal and distal angles 256, 258 of articulation equal when articulating the bending section 212: (i) ratioed pulleys/capstans in the articulation handle 214, and (ii) articulation holes for receiving articulation cables (pull wires) that have different radii but the same angle in the bending sections. First, however, the relation between the pull wires 236 and the bending section 212 will be described with reference to FIGS. 24A and 24B.

Figure 24A:
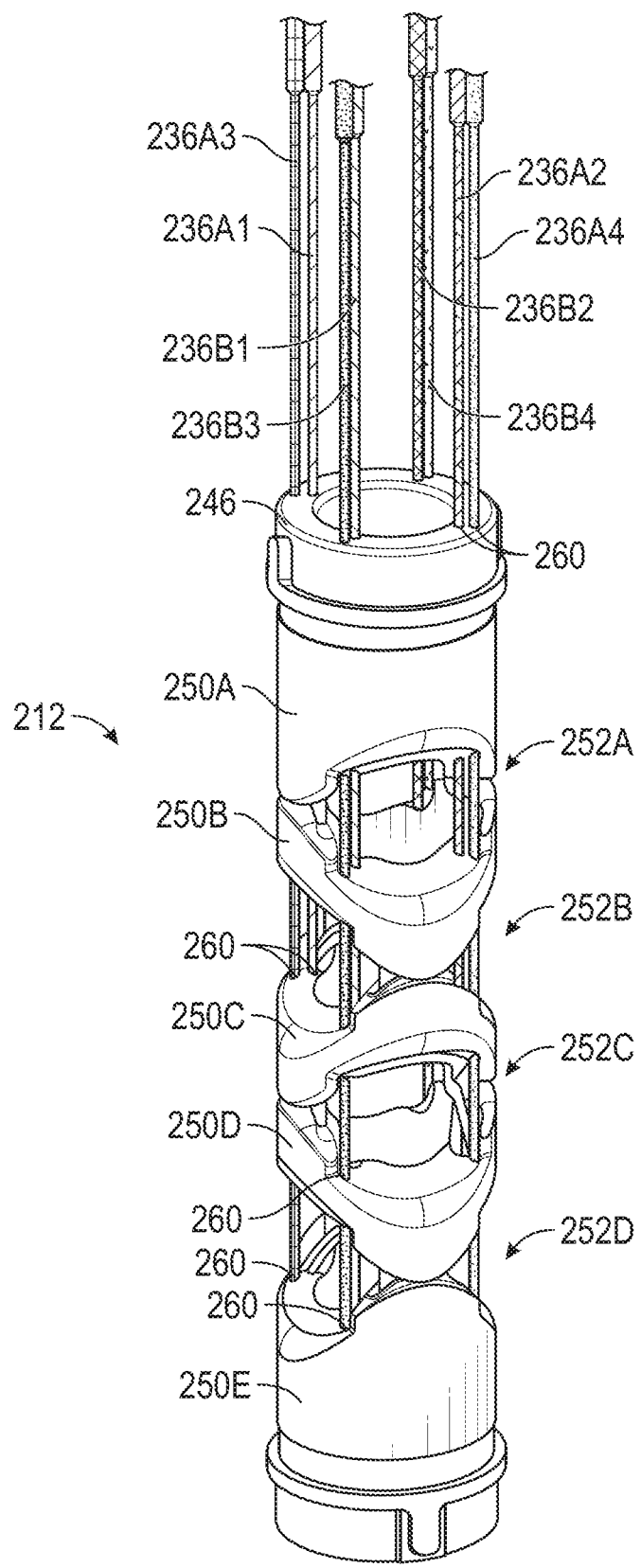
FIGS. 24A and 24B are perspective proximal and distal views, respectively, of an embodiment of a bending section and associated pull wires for an articulating medical instrument.
Figure 24B:
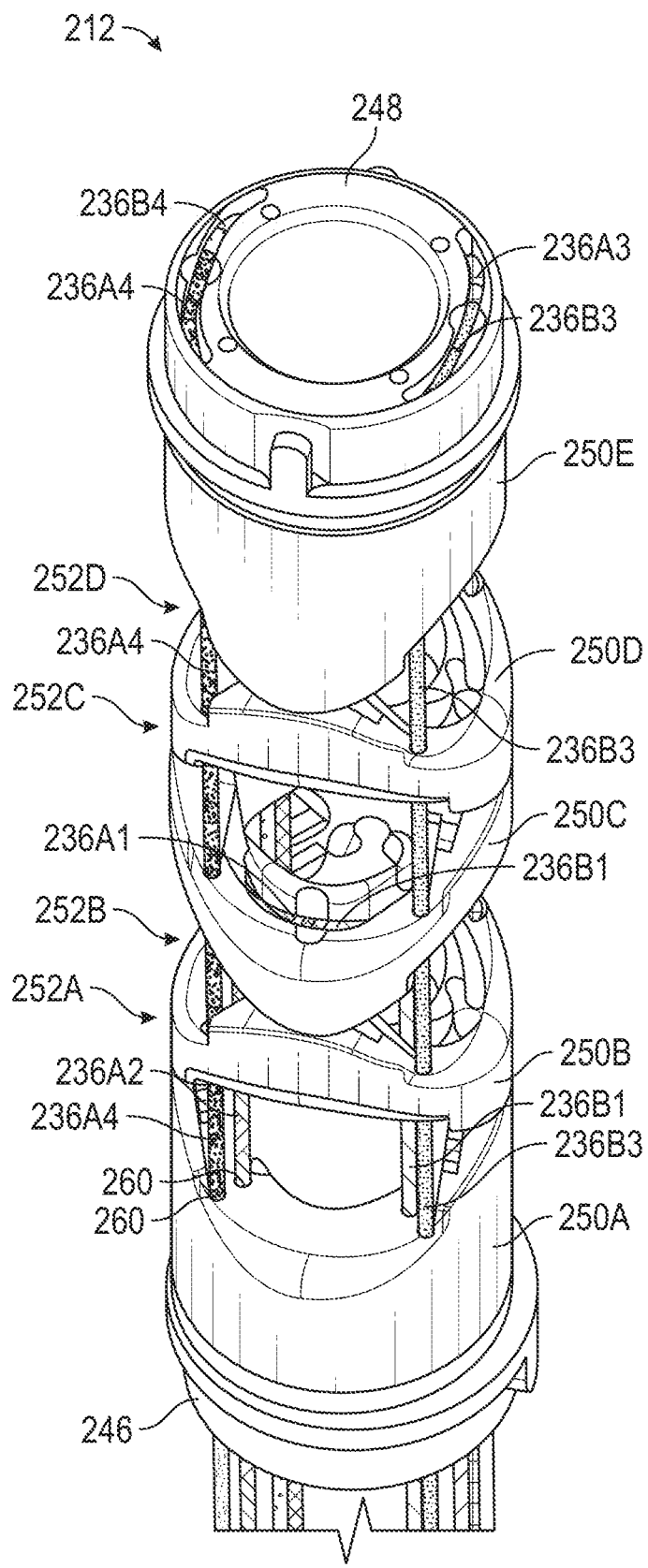

FIG. 24A illustrates a proximal perspective view of the bending section 212 and pull wires 236. FIG. 24B illustrates a distal perspective view of the bending section 212 and the pull wires 236. Hatching patterns of the pull wires 236 is consistent with the hatching patterns used in FIGS. 22B and 22C.

In the illustrated embodiment, the pull wires 236 extend through the distal end 206 of the bending section 212 and through one or more links 250 of the bending section 212. The pull wires 236 can extend through articulation holes 260 in the links 250. Examples of the articulation holes 260 are shown in greater detail in FIGS. 26A-26C described below. In FIGS. 24A and 24B, not every articulation hole 260 is labeled for clarity.

In the illustrated embodiment, the third pull wires 236A3, 236B3 and the fourth pull wires 236A4, 236B4 extend through each of the links 250. Specifically, the third pull wires 236A3, 236B3 and the fourth pull wires 236A4, 236B4 extend from the proximal end 246 of the bending section 212, through the first link 250A, the second link 250B, the third link 250C, the fourth link 250D, and the fifth link 250E. At the distal end 248 of the bending section 212, as shown in FIG. 24B, the third pull wires 236A3, 236B3 can be attached to each other with crimp, and the fourth pull wires 236A4, 236B4 can be attached to each other with a crimp. In some embodiments, the third pull wires 236A3, 236B3 need not be attached to each other, and the fourth pull wires 236A4, 236B4 need not be attached to each other. For example, in some embodiments, the distal ends of the third pull wires 236A3, 236B3 each end in a crimp (and are not attached to each other), and the fourth pull wires 236A4, 236B4 each end in a crimp (and are not attached to each other).

As illustrated, the third pull wires 236A3, 236B3 are positioned on a first lateral side of the bending section 212, and the fourth pull wires 236A4, 236B4 are positioned on a second lateral side of the bending section 212 that is opposite the first lateral side. In this configuration, pulling (spooling) the third pull wires 236A3, 236B3 (and correspondingly, releasing (unspooling) the fourth pull wires 236A4, 236B4) causes the bending section to articulate toward the first lateral side. For example, in some embodiments, pulling the third pull wires 236A3, 236B3 causes the bending section 212 to articulate in a first direction. Similarly, pulling (spooling) the fourth pull wires 236A4, 236B4 (and correspondingly, releasing (unspooling) the third pull wires 236A3, 236B3) causes the bending section 212 to articulate toward the second lateral side. For example, in some embodiments, pulling the fourth pull wires 236A4, 236B4 causes the bending section 212 to articulate in a second direction, opposite the first direction. More specifically, in the illustrated embodiment, pulling the third pull wires 236A3, 236B3 causes the second joint 252B and the fourth joint 252D to articulate in the first direction, and pulling the fourth pull wires 236A4, 236B4 causes the second joint 252B and the fourth joint 252D to articulate in the second direction. In this example, the first and second directions can be first and second pitch or yaw directions.

In the illustrated embodiment, the first pull wires 236A1, 236B1 and the second pull wires 236A2, 236B2 extend through only some of the links 250. Specifically, the first pull wires 236A1, 236B1 and the second pull wires 236A2, 236B2 extend from the proximal end 246 of the bending section 212, through the first link 250A, the second link 250B, and the third link 250C. At the distal end 248 of the third link 250C, as shown in FIG. 24B, the first pull wires 236A1, 236B1 can be attached to each other with crimp. Although not visible in FIG. 24B, at the distal end 248 of the third link 250C and on the opposite side, the second pull wires 236A2, 236B2 can be attached to each other with a crimp. In some embodiments, the first pull wires 236A1, 236B1 need not be attached to each other, and the second pull wires 236A2, 236B2 need not be attached to each other. For example, in some embodiments, the distal ends of the first pull wires 236A1, 236B1 each end in a crimp (and are not attached to each other), and the second pull wires 236A2, 236B2 each end in a crimp (and are not attached to each other).

As illustrated, the first pull wires 236A1, 236B1 are positioned on a third lateral side of the bending section 212, and the second pull wires 236A4, 236B4 are positioned on a fourth lateral side of the bending section 212 that is opposite the first lateral side. In this configuration, pulling (spooling) the first pull wires 236A1, 236B1 (and correspondingly, releasing (unspooling) the second pull wires 236A2, 236B2) causes the bending section 212 to articulate toward the third lateral side. For example, in some embodiments, pulling the first pull wires 236A1, 236B1 causes the bending section 212 to articulate in a third direction. Similarly, pulling (spooling) the second pull wires 236A2, 236B2 (and correspondingly, releasing (unspooling) the first pull wires 236A1, 236B2) causes the bending section to articulate toward the fourth lateral side. For example, in some embodiments, pulling the third pull wires 236A2, 236B2 causes the bending section 212 to articulate in a fourth direction, opposite the third direction. More specifically, in the illustrated embodiment, pulling the first pull wires 236A1, 236B1 causes the first joint 252A and the third joint 252C to articulate in the third direction, and pulling the second pull wires 236A2, 236B2 causes the first joint 252A and the third joint 252C to articulate in the fourth direction. In this example, the third and fourth directions can be first and second pitch or yaw directions.

As mentioned above, in some embodiments, the medical instrument 200 can include two unique cooperating features that help to keep the proximal and distal angles of articulation 256, 258 (see FIG. 23B) equal when articulating the bending section 212: (i) ratioed capstans or pulleys 234 in the articulation handle 214, and (ii) articulation holes 260 in the links 250 for receiving pull wires 234 that have different radii but the same angle in the bending section 212. Examples of these features are described in the following subsections.

(i) Ratioed Pulleys/Capstans in the Articulation Handle

In the illustrated embodiment, the medical instrument 200 includes pulleys 234, as shown for example in FIGS. 22A-22C. In some embodiments, the pulleys 234 can be configured such that ratios between the diameters of certain of the pulleys 234 are set to enable the proximal and distal angles of articulation 256, 258 (see FIG. 23B) to be equal or substantially equal during articulation of the bending section 212. This is referred to herein as "ratioed pulleys."

Figure 25:
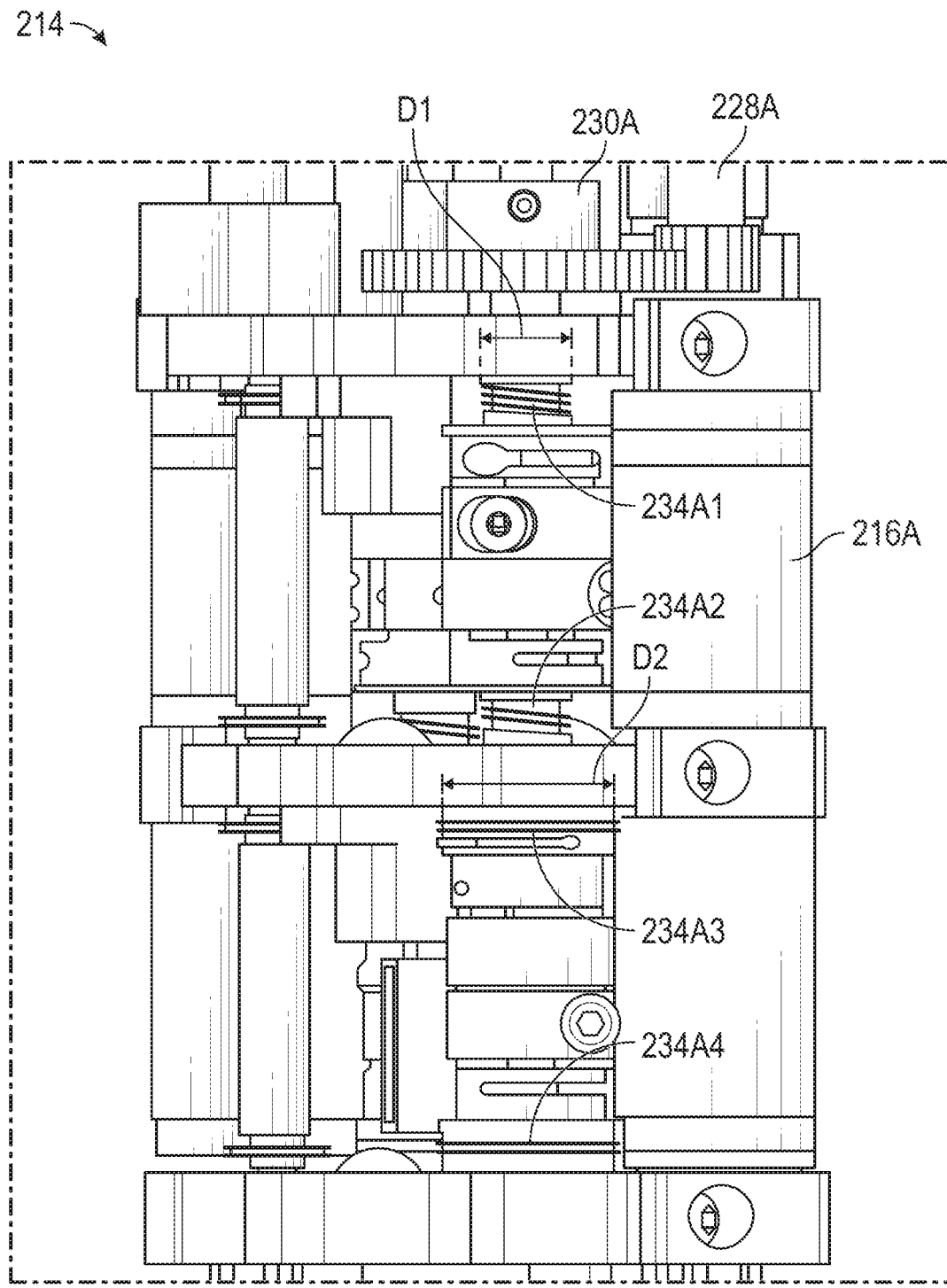
FIG. 25 illustrates an embodiment of an articulation handle including ratioed pulleys.

FIG. 25 illustrates four of the pulleys 234: the first pulley 234A1, the second pulley 234A2, the third pulley 234A3, and the fourth pulley 234A4. These pulleys 234 are associated with the pull wires 236 as shown in FIGS. 22B and 22C. The pull wires 236 are further connected to the bending section 212 as shown in FIGS. 24A and 24B. As shown, the first pulley 234A1 and the second pulley 234A2 each comprise a first diameter D1. The third pulley 234A3 and the fourth pulley 234A4 each comprise a second diameter D2. As illustrated, for some embodiments, the diameter D2 is larger than the diameter D1. The pulleys 234 may be configured such that the ratio of D2 to D1 facilitates maintaining equal proximal and distal angles of articulation (e.g., pitch or yaw).

The advantage of providing ratioed pulleys 234 is that the ratioed pulleys can help to constrain the cable or pull wire path length to the proximal and distal joints 250 of the bending section, such that their articulation angles are substantially equivalent. For example, the ratioed pulleys help to maintain a substantially constant articulation angle between the proximal and distal articulation joints 250. In some embodiments, the ratio of the diameters of the distal pulleys (i.e., the third and fourth pulleys 234A3, 234A4) to the proximal pulleys (i.e., the first and second pulleys 234A1, 234A2) can be greater than or equal to 1.5:1, 1.75:1, 2:1, or 2:25:1.

In some embodiments, the ratioed pulleys 234 can enable substantially equal proximal and distal articulation angles because, for a given rotation, the larger pulleys 234 unspool or spool more of the pull wires 236 than the smaller pulleys 234. This allows more pull wire length to be unspooled for the pull wires 236 that extend through all of the links 250 of the bending section than for the pull wires 236 that extend through only some of the links of the bending section 250. The ratioed pulleys 234 thus advantageously help maintain equal proximal and distal angles of articulation (e.g., proximal/distal pitch and proximal/distal yaw).

(ii) Articulation Holes with Different Radii but Same Angle

Figure 26B:
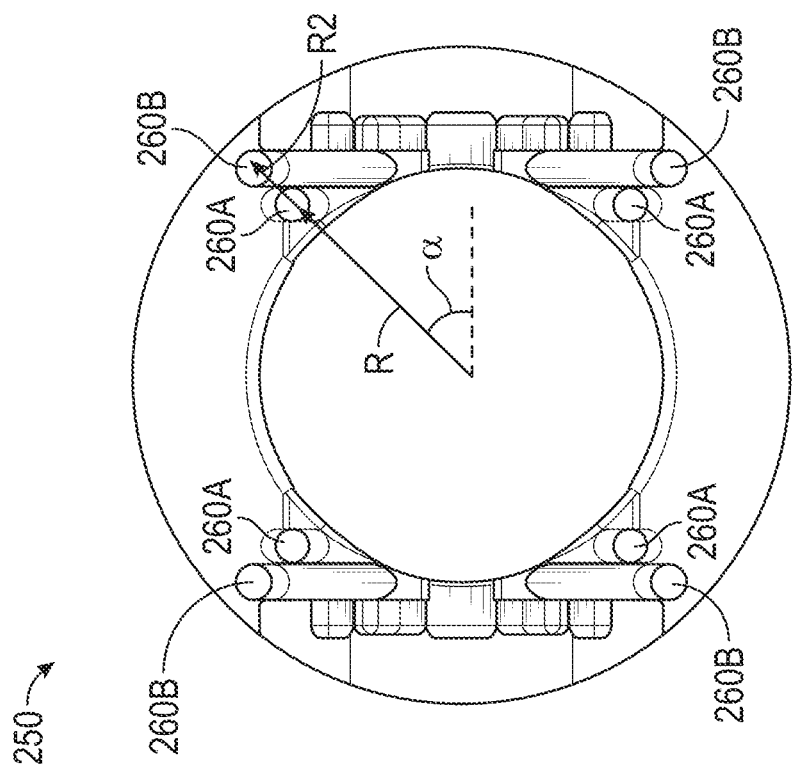
FIGS. 26A-26D illustrate arrangements of articulation holes in embodiments of links of a bending section of an articulating medical instrument.
Figure 26A:
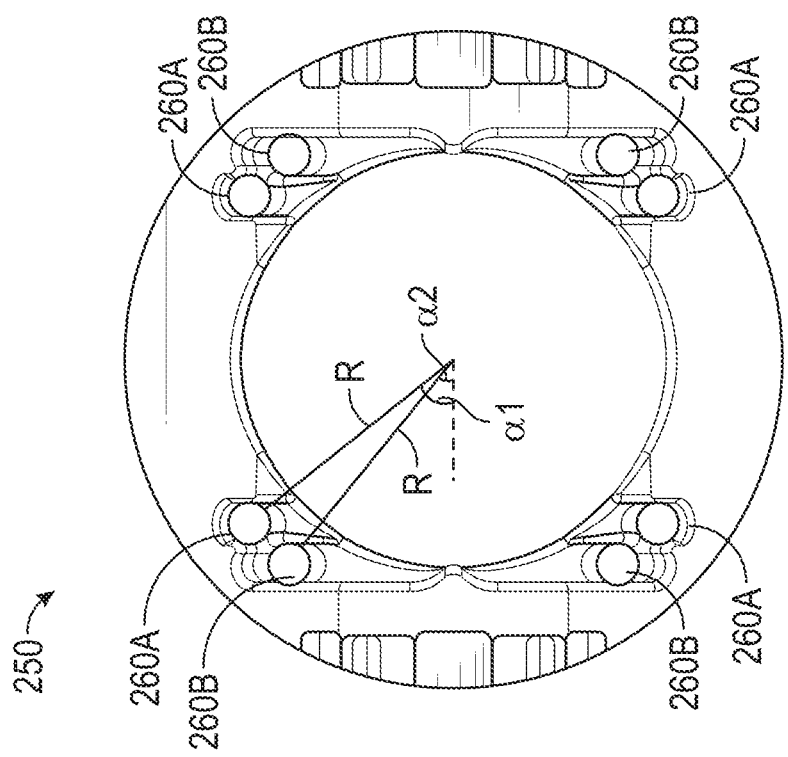

In some embodiments, the medical instrument 200 is further configured such that the articulation holes 260 through which the pull wires 236 pass through the links 250 of the bending section 212 are arranged at different radii but the same angle (as shown in FIG. 26B) instead of on a constant radius but different angles (as shown in FIG. 26A). For example, in some embodiments, to maintain equal proximal and distal angles of articulation, it may be desirable to configure the articulation holes 260 on the links 250 such that the ratio of the distance from the midline to articulation holes 260 is the same in pitch and yaw. This may allow coordinated motion between the two pull wires 236 that are running next to each other in order provide pure pitch or yaw motion.

As noted above, some of the pull wire pairs 236 terminate at the middle or third link 250C, while other pairs terminate at the distal or fifth link 250E (see FIGS. 24A and 24B). In some embodiments, to maintain constant angles of proximal and distal articulation, the ratio of the distance the pull wire 236 is pulled divided by the radius of the articulation hole 260 from the axis of bending can be 2:1 for the further terminating pull wires 236 to the middle terminating pull wires 236. This is because the further terminating pull wires 236 go through two angle segments, and the middle terminating pull wires 236 only go through one. In some embodiments, it may be challenging to satisfy the constraint for both pitch and yaw unless the radius to both the pitch and yaw axis are substantially equal, hence the use of the radial design.

An embodiment of a link having articulation holes on a constant radius, but different angle, is shown in FIG. 26A. In this embodiment, articulation holes 260 are labeled 260A for holes associated with pull wires 236 that terminate at the distal link 250E, and 260B for holes associated with pull wires 236 that terminate at the middle link 250C. As shown, each hole 260A, 260B is positioned on the link 250 at the same radius R, but at different angles a1, a2. In this embodiment, because the articulation holes 260A, 260B are positioned at the same radius R, but different angles α1, α2, the bending section 212 might not exhibit even bending between the pitch and yaw direction. In such embodiments, software may need to compensate for the discrepancy between pitch and yaw articulations in this embodiment.

For even bending between pitch and yaw directions, while maintaining substantially equal proximal and distal articulation, the links 250 can be configured as shown in FIG. 26B. This embodiment of the link 250 includes articulation holes 260A, 260B, which are formed at the same angle a, but different radii R1, R2. In conjunction with the ratioed pulleys 234 described above, these links 250 of the bending section 212 may exhibit desirable bending characteristics. In some embodiments, the advantage the having articulation holes 260A, 260B having different radii R1, R2 but the same angle a is that the distance from an articulation midline to the articulation holes 260 can be the same for pitch and yaw.

Figure 26D:
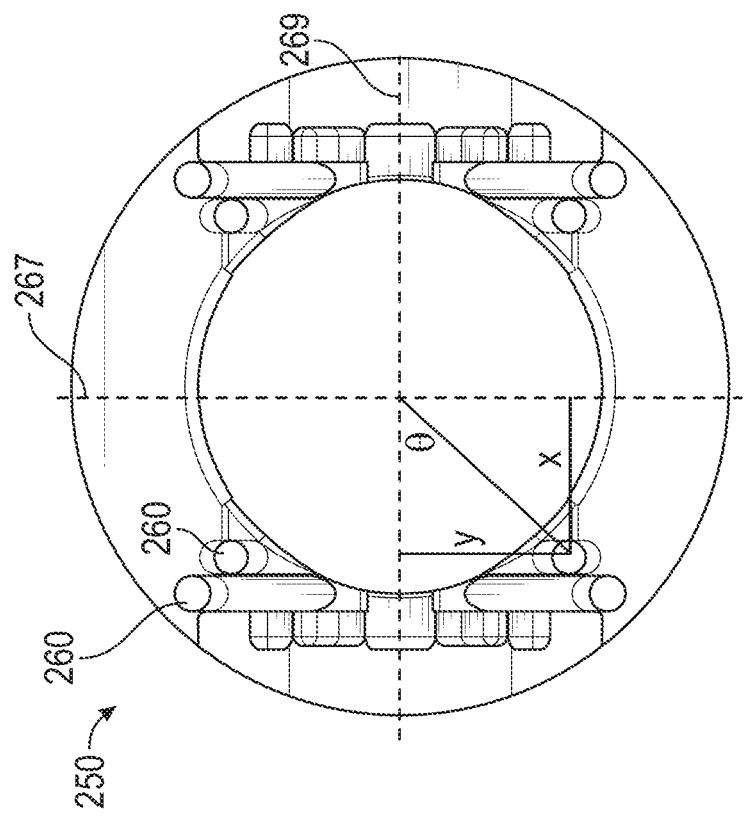
Figure 26C:
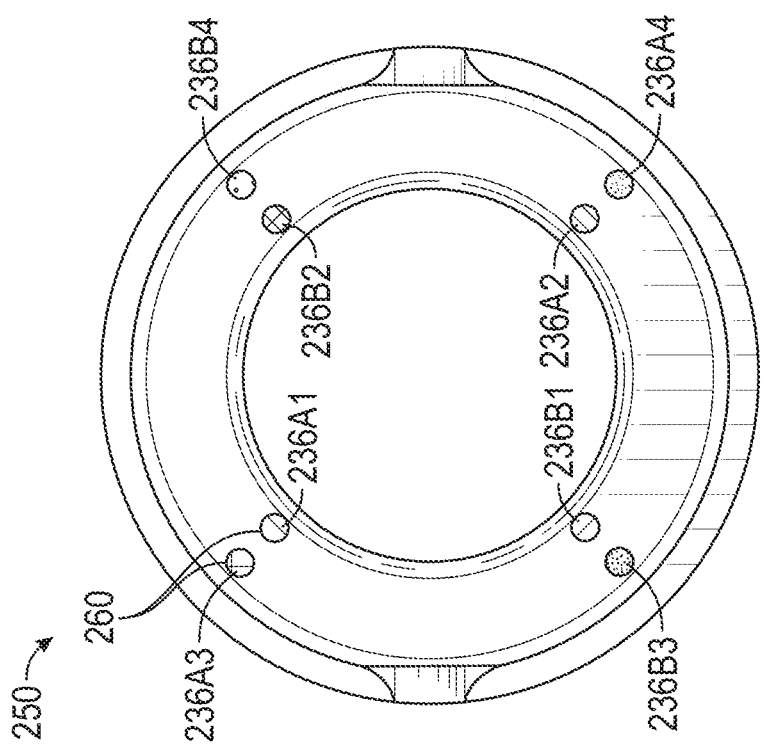

FIG. 26C illustrates an example of the arrangement of the pull wires 236 within the articulation holes 260 of a link 250 configured with articulation holes 260A, 260B having different radii R1, R2 but the same angle α, as shown in FIG. 26B. Color coding in FIG. 26C is consistent with the color coding in FIGS. 22B and 22C and FIGS. 24A and 24B.

FIG. 26D illustrates the improved link 250 in FIG. 26B having articulation holes with different radii but same angle with a sample pitch articulation midline and yaw articulation midline. From this view, one can see the advantages that are obtained from having articulation holes with different radii but same angle. In each quadrant, a pair of articulation holes 260 are in-line, in the same angular position θ, but with different radii. Regardless of whether the bending section 212 is pitched or yawed, each of the articulation holes 260 will have a distance x from the pitch articulation midline and a distance y from the yaw articulation midline, whereby x and y are equal. The advantage of providing such articulation holes 260 is that you can maintain coordinated motion between two cable segments that are running next to each other in order to provide pure pitch or yaw motion. In contrast, if the articulation holes 260 have the same radii but different angle (e.g., as shown in FIG. 26A), software might need to be used to compensate for the discrepancy between the pitch and yaw articulations Advantageously, the link 250 design shown in FIGS. 26B-26D, which includes articulation holes 260 formed at the same angle a, but different radii R1, R2, may provide a more deterministic driving experience and a more stable bending section than other devices.

C. Additional Embodiments of Articulating Medical Instruments

Figure 28:
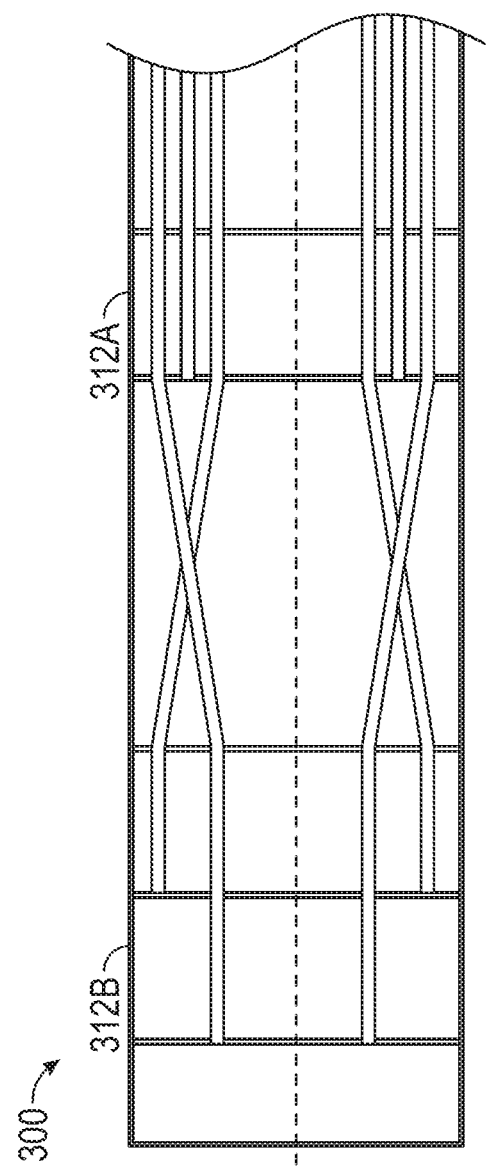
FIG. 28 illustrates an example arrangement of pull wires for the articulating medical instrument of FIGS. 27A and 27B.

The articulating medical instrument 200 in the illustrated embodiments described above includes a wrist having multiple degrees of freedom (e.g., proximal pitch, distal pitch, proximal yaw, distal yaw) that can be articulated using one or more motors 216. While it is believed that this architecture provides a clinician sufficient dexterity to accomplish most if not all viewings during laparoscopic medical procedures, other embodiments for articulating medical instruments also are possible. In some embodiments, it is possible to have an instrument that includes a six degree of freedom link architecture constrained into two degree of freedom bending sections and controlled by a total of four motors. Such an embodiment is illustrated in FIGS. 27A-28.

FIGS. 27A and 27B illustrate embodiment of a medical instrument 300 that includes more than one bending section. For example, as illustrated, the medical instrument 300 includes a first bending section 312A and a second bending section 312B. In some embodiments, the second bending section 312B can include a four degree of freedom link segment constrained into a two degree of freedom wrist at a distal end of the medical instrument 300, and the first bending section 312A may comprise a two degree of freedom segment constrained into a separate two degree of freedom wrist. With this configuration, a surgeon may be able to command the medical instrument to a side and then be able to look back without having large angulations outside of the body (i.e., the position illustrated in FIG. 27A).

In some embodiments, in order for the medical instrument 300, having a first bending section 312A (e.g., two degrees of freedom) and a second bending section 312B (e.g., four degrees of freedom) to function, pull wires for driving the second bending section 312B should pass through the first bending section 312A in a way that allows articulation of the second bending section 312B without affecting the articulation of the first bending section 312A, and vice versa. In some embodiments, this may be accomplished by routing distally extending pull wires through the first bending section 312a in a way such that their path length does not change under articulation. In another embodiment, the distally extending pull wires can be routed through the first bending section 312A such that one can compensate for the change in path length. The change in path length can be compensated, in some embodiments, by the same ratio as is used to drive the constraint in 312B. This can be achievable not only by using the ratioed pulleys and articulation holes with different radii but the same angle as discussed above, but also by providing "cross-over" pull wires as shown in FIG. 28.

It has been determined by the present inventors, that the pull wires that extend/terminate at a distal link of the second bending section 312B are best routed along the outside of the links of the first bending section 312A, and then cross-over towards the inside of the second bending section 312B. The pull wires that extend/terminate at a mid-link of the second bending section 312B are best routed along the inside of the links of the first bending section 312A, and then cross-over towards the outside of the second bending section 312B. By doing this, one minimizes the ratio of distances needed to achieve a proper coupling. This may be desirable because a goal may be to maximize the amount of space in the middle lumen for payload and also to maximize the radius of the pull wires for higher leverage under articulation.

To this end, the center lumen may be maximized when the ratio of distances is equal for the second bending section 312B as it is for the first bending section 312A that is passed through. It has been found that when this is done, the ratio will be the square root of two. This means that the ratio of the pulley diameters and the ratio of the distances on the radius will be matched at a square root of two. FIG. 28 illustrates a schematic of cross-cabling for the medical instrument 300 constrained with a square root of two ratio. Note that a third set of pull wires (e.g., that do not cross or reroute) terminate at the proximal articulation section and drive the articulation of these links.

In addition, in some embodiments, rather than providing an articulating medical instrument 200 with a rolling snake wrist design, as shown and described above, the insertion handle architecture can be implemented with a pivot based (i.e., non-snake wrist) bending section. In such embodiment, the articulation handle may have fewer pulleys (e.g., 2 pulleys) on each output shaft because fewer cable segments (e.g., 4 cable segments) would be driven.

3. Implementing Systems and Terminology

Implementations disclosed herein provide systems, methods and apparatus related to articulating medical instruments.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The any processor implemented functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method, comprising:
   inserting a distal end of a medical instrument comprising an elongate shaft into a treatment area of a patient; and
   articulating a first bending section of the medical instrument by driving one or more motors positioned within an articulation handle positioned at a proximal end of the elongated shaft, wherein the articulation handle comprises a pitch motor, driving the one or more motors positioned within the articulation handle comprises using the pitch motor to drive a proximal pitch pulley connected to a proximal pitch joint of the first bending section by a first pull wire, and a proximal pitch pulley radius of the proximal pitch pulley is different than a distal pitch pulley radius of a distal pitch pulley.

2. The method of claim 1, wherein the method further comprises driving the one or more motors positioned within the articulation handle, wherein driving the one or more motors positioned within the articulation handle comprises using the pitch motor to drive a distal pitch pulley connected to a distal pitch joint of the first bending section by a second pull wire.

3. The method of claim 2, wherein the pitch motor is configured to drive the proximal pitch pulley and the distal pitch pulley such that rotation of the proximal pitch pulley is of substantially equal rotation to the distal pitch pulley.

4. The method of claim 3, wherein a ratio between the distal pitch pulley radius and the proximal pitch pulley radius is such that an articulation of the proximal pitch joint is substantially equal to an articulation of the distal pitch joint.

5. The method of claim 2, wherein driving the one or more motors positioned within the articulation handles further comprises:
   driving, with a yaw motor, a proximal yaw pulley operably connected to a proximal yaw joint of the first bending section by a third pull wire, and a distal yaw pulley operably connected to a distal yaw joint of the first bending section by a fourth pull wire, wherein a distal yaw pulley radius of the distal yaw pulley is different than a proximal yaw pulley radius of the proximal yaw pulley.

6. The method of claim 5, wherein the yaw motor is configured to drive the proximal yaw pulley and the distal yaw pulley such that rotation of the proximal yaw pulley is of substantially equal rotation to the distal yaw pulley.

7. The method of claim 6, wherein a ratio between the distal yaw pulley radius and the proximal yaw pulley radius is such that an articulation of the proximal yaw joint is equal to an articulation of the distal yaw joint.

8. The method of claim 2, wherein articulating the first bending section comprises:
   pulling the first pull wire that passes through a first articulation hole in a link of the first bending section; and
   pulling the second pull wire that passes through a second articulation hole in the link of the first bending section, wherein the first articulation hole and the second articulation hole are formed at a same angle relative to a central axis through the link and comprise different radii measured from the central axis.

9. The method of claim 8, wherein:
   pulling the first pull wire comprises rotating the proximal pitch pulley on which the first pull wire is wound; and
   pulling the second pull wire comprises rotating the distal pitch pulley on which the second pull wire is wound, wherein the distal pitch pulley radius of the distal pitch pulley is greater than the proximal pitch pulley radius of the proximal pitch pulley.

10. The method of claim 9, wherein the proximal pitch pulley and the distal pitch pulley are driven by the same motor such that rotation of the proximal pitch pulley is equal to rotation of the distal pitch pulley.

11. The method of claim 1, further comprising articulating a second bending section on the elongate shaft of the medical instrument by driving one or more motors positioned within the articulation handle, wherein the second bending section is positioned between the first bending section and the proximal end of the elongate shaft.

12. A method, comprising:
    articulating a first bending section of a medical instrument by pulling a proximal pitch joint of the first bending section via a first pull wire; and articulating the first bending section of the medical instrument by pulling a distal pitch joint of the first bending section via a second pull wire, wherein articulating the first bending section comprises:
  pulling the first pull wire that passes through a first articulation hole in a link of the first bending section; and
  pulling the second pull wire that passes through a second articulation hole in the link of the first bending section,
  wherein the first articulation hole and the second articulation hole are formed at a same angle relative to a central axis through the link and comprise different radii measured from the central axis.

13. The method of claim 12, wherein:
pulling the first pull wire comprises rotating a proximal pulley on which the first pull wire is wound; and
pulling the second pull wire comprises rotating a distal pulley on which the second pull wire is wound,
wherein a distal pulley radius of the distal pulley is greater than a proximal pulley radius of the proximal pulley.

14. The method of claim 13, wherein the proximal pulley and the distal pulley are driven by the same motor such that rotation of the proximal pulley is equal to rotation of the distal pulley.

15. The method of claim 12, further comprising articulating a second bending section on a shaft of the medical instrument, wherein the second bending section is positioned between the first bending section and the proximal end of the shaft.

16. A method, comprising:
inserting a distal end of a medical instrument comprising an elongate shaft into a treatment area of a patient;
articulating a first bending section of the medical instrument via one or more motors disposed within an articulation handle;
using the one or more motors to drive a proximal pitch pulley connected to a proximal pitch joint of the first bending section by a first pull wire, wherein a proximal pitch pulley radius of the proximal pitch pulley is different than a distal pitch pulley radius of a distal pitch pulley; and
translating the elongate shaft via an insertion handle, wherein the elongate shaft translates relative to the insertion handle.

17. The method of claim 16, further comprising translating the elongate shaft via an instrument drive mechanism coupled to the articulation handle.

18. The method of claim 17, further comprising engaging at least one drive output of the instrument drive mechanism via at least one drive input of the articulation handle.

19. A method, comprising:
inserting a distal end of a medical instrument comprising an elongate shaft into a treatment area of a patient; and
articulating a first bending section of the medical instrument by driving one or more motors positioned within an articulation handle positioned at a proximal end of the elongated shaft, wherein the articulation handle comprises a pitch motor, driving the one or more motors positioned within the articulation handles comprises using the pitch motor to drive a distal pitch pulley connected to a distal pitch joint of the first bending section by a pull wire, and a distal pitch pulley radius of the distal pitch pulley is different than a proximal pitch pulley radius of a proximal pitch pulley.

* * * * *